US009579315B2

(12) United States Patent
Liggett et al.

(10) Patent No.: US 9,579,315 B2
(45) Date of Patent: Feb. 28, 2017

(54) METHODS OF TREATING OBSTRUCTIVE LUNG DISEASES USING BITTER TASTANTS

(75) Inventors: Stephen B. Liggett, Baltimore, MD (US); Wayne C. H. Wang, Ellicott City, MD (US); Deepak A. Deshpande, Ellicott City, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 13/812,508

(22) PCT Filed: Jul. 27, 2011

(86) PCT No.: PCT/US2011/045537
§ 371 (c)(1),
(2), (4) Date: Jan. 26, 2013

(87) PCT Pub. No.: WO2012/021291
PCT Pub. Date: Feb. 16, 2012

(65) Prior Publication Data
US 2013/0131108 A1  May 23, 2013

Related U.S. Application Data

(60) Provisional application No. 61/371,946, filed on Aug. 9, 2010, provisional application No. 61/405,883, filed on Oct. 22, 2010.

(51) Int. Cl.
| | | |
|---|---|---|
| A61K 31/4706 | (2006.01) | |
| A61K 31/24 | (2006.01) | |
| A61K 31/428 | (2006.01) | |
| A61K 31/165 | (2006.01) | |
| A61K 31/167 | (2006.01) | |
| A61K 31/4745 | (2006.01) | |
| A61K 31/475 | (2006.01) | |
| A61K 31/49 | (2006.01) | |
| A61K 31/7034 | (2006.01) | |
| G01N 33/50 | (2006.01) | |
| A61K 31/36 | (2006.01) | |
| A61K 9/00 | (2006.01) | |

(52) U.S. Cl.
CPC ........ *A61K 31/4706* (2013.01); *A61K 31/165* (2013.01); *A61K 31/167* (2013.01); *A61K 31/24* (2013.01); *A61K 31/36* (2013.01); *A61K 31/428* (2013.01); *A61K 31/475* (2013.01); *A61K 31/4745* (2013.01); *A61K 31/49* (2013.01); *A61K 31/7034* (2013.01); *G01N 33/5061* (2013.01); *A61K 9/0073* (2013.01); *G01N 2800/122* (2013.01)

(58) Field of Classification Search
IPC ........................ A61K 31/4706,31/428, 31/24
See application file for complete search history.

(56) References Cited

U.S. PATENT DOCUMENTS

| | | | |
|---|---|---|---|
| 6,572,858 B1 * | 6/2003 | Charous | 424/184.1 |
| 7,294,474 B2 | 11/2007 | Zoller et al. | |
| 7,364,867 B2 | 4/2008 | Margolskee et al. | |
| 7,794,959 B2 * | 9/2010 | Li et al. | 435/7.21 |
| 2004/0208833 A1 * | 10/2004 | Hovey et al. | 424/46 |
| 2005/0100885 A1 * | 5/2005 | Crooke et al. | 435/5 |
| 2006/0198896 A1 * | 9/2006 | Liversidge et al. | 424/489 |
| 2009/0054381 A1 * | 2/2009 | Letts | A61K 31/34 514/171 |
| 2009/0074894 A1 | 3/2009 | Li et al. | |
| 2009/0087866 A1 | 4/2009 | Li et al. | |
| 2010/0272811 A1 * | 10/2010 | Scher | A61K 31/46 424/489 |

FOREIGN PATENT DOCUMENTS

WO  97-09046 A1  3/1997
WO  WO 2008/141438 A1 * 11/2008

OTHER PUBLICATIONS

Shah et al. (Science 325, 1131-1134 (2009).*
Cohen et al.( American Review of Respiratory Disease, vol. 143, No. 5_pt_1 (1991), pp. 1038-1043).*
Nolte et al. (Journal of Chemical Ecology, vol. 20, No. 2, 1994.*
Chandrashekar et al. ( Cell, vol. 100, 703-711, Mar. 17, 2000).*
Deshpande et al. (Nature Medicine 16, (1299-1304); 2010).*
Meyerhof et al. (Chem. Senses 35: 157-170, 2010 ).*
International Search Report issuing in PCT/US2011/045537 on Mar. 27, 2012.

* cited by examiner

*Primary Examiner* — Shirley V Gembeh
(74) *Attorney, Agent, or Firm* — Wenderoth, Lind & Ponack, L.L.P.

(57) ABSTRACT

Described herein are methods for enhancing airway dilation and/or relieving bronchoconstriction, e.g., to treat obstructive lung diseases such as asthma and COPD, by administering bitter tastants to subjects in need thereof. Also described herein are methods for identifying compounds that modulate function of bitter tastant receptors.

20 Claims, 17 Drawing Sheets

[Ca$^{2+}$]$_i$ responses to the bitter tastant chloroquine
in human airway smooth muscle cells

[Ca$^{2+}$]$_i$ responses to the bitter tastant chloroquine
in human airway smooth muscle cells

[Ca$^{2+}$]$_i$ responses to bitter tastants in H292 cells

[Ca$^{2+}$]$_i$ responses to bitter tastants in H292 cells

[Ca$^{2+}$]$_i$ responses to bitter tastants in H292 cells

[Ca$^{2+}$]$_i$ responses to choroquine in the human
lung airway non-ciliated epithelial cell line BEAS-2B $[Ca^{2+}]_i$ responses to choroquine in the human
lung airway non-ciliated epithelial cell line BEAS-2B

METHODS OF TREATING OBSTRUCTIVE LUNG DISEASES USING BITTER TASTANTS

STATEMENT REGARDING FEDERALLY SPONSORED RESEARCH

This invention was made with government support under Grant Numbers HL045967 and HL071609 awarded by the National Institutes of Health. The government has certain rights in the invention.

FIELD

Provided herein are methods for increasing airway dilation and/or reducing airway constriction, e.g., to treat obstructive lung disease, by administering compounds that bind to bitter tastant receptors expressed on the surface of airway smooth muscle cells. Also provided herein are methods of identifying compounds that modulate function of bitter tastant receptors.

BACKGROUND

Asthma and chronic obstructive pulmonary disease (COPD) together affect 300 million individuals worldwide. The major source of morbidity and mortality from both diseases is airway obstruction, which often is due to actively constricted smooth muscle of the bronchi/bronchial tree[1]. Although airway resistance in COPD has variable degrees of reversibility due to structural changes from smoking, therapies for COPD and asthma both include antagonists directed to broncho-constrictive receptors, and agonists directed to receptors that relax airway smooth muscle (ASM)[2,3].

The major receptor signaling family of ASM that regulates contraction and relaxation are G-protein coupled receptors (GPCRs)[3]. There is an ongoing effort to identify GPCR pathways leading to regulation of airway tone, thereby providing for new treatment strategies for asthma and COPD. Such efforts are needed because the incidence of both diseases is increasing and at least one-half of all patients are not well controlled with currently available agents[4,5].

There is an unmet need for additional therapeutic options in the treatment of obstructive airway diseases such as asthma and COPD. While there has been some progress in refining drugs that antagonize a particular $G_q$-coupled pathway, thereby potentially decreasing bronchospasm, β-agonists remain the only practical direct bronchodilators. The discovery and development of new means for treating obstructive lung diseases, such as asthma and COPD, are urgently needed.

SUMMARY

In a first aspect, provided herein are methods of treating an obstructive lung disease or condition in a subject, comprising administering a therapeutically effective amount of a pharmaceutical composition comprising a bitter tastant to a subject in need of treatment. In particular aspects, the obstructive lung disease or condition can be, e.g., asthma, chronic obstructive pulmonary disease (COPD), emphysema or bronchitis.

In a second aspect, provided herein are methods of inducing bronchodilation in a subject, comprising administering a therapeutically effective amount of a pharmaceutical composition comprising a bitter tastant to a subject in need of bronchodilation.

In a third aspect, provided herein are methods of relaxing airway smooth muscle (ASM) in a subject, comprising administering a therapeutically effective amount of a pharmaceutical composition comprising a bitter tastant to a subject in need of ASM relaxation.

In a fourth aspect, provided herein are methods of treating or preventing bronchoconstriction or bronchospasm in a subject, comprising administering a therapeutically effective amount of a pharmaceutical composition comprising a bitter tastant to a subject in need of treatment or prevention of bronchoconstriction or bronchospasm.

In particular aspects of the above-described methods, the bitter tastant can be a compound such as aristocholic acid, chloroquine, colchicine, denatonium, quinine, saccharin, salicin, strychnine or yohimbine. In yet other aspects of the above-described methods, the pharmaceutical composition can be in the form of an inhalant or other delivery method, such as oral delivery, and the subject can be a human or other animal.

In a fifth aspect, provided herein are methods for identifying a compound for relaxing airway smooth muscle, comprising contacting an airway smooth muscle cell with a test compound that binds to a bitter tastant receptor and determining whether the test compound relaxes the airway smooth muscle cell, wherein a compound that relaxes the smooth muscle cell is identified as a compound for relaxing airway smooth muscle. For example, relaxation of the airway smooth muscle cell can be detected by detecting an increase in bitter tastant receptor-mediated signaling in the airway smooth muscle cell, e.g., by detecting an increase in intracellular calcium release or an increase in intracellular IP3 in the airway smooth muscle cell.

In a sixth aspect, provided herein are methods for identifying a modulator of a bitter taste receptor, comprising contacting an airway cell that naturally expresses a bitter taste receptor with a test compound, and measuring the activity of the bitter taste receptor, wherein a compound that increases activity of the bitter taste receptor is an agonist of the bitter taste receptor and a compound that decreases activity of the bitter taste receptor is an antagonist of the bitter taste receptor. For example, a change in activity of the bitter tastant receptor is detected by a change in intracellular calcium release or a change in intracellular IP3 in the airway smooth muscle cell, relative to an airway smooth muscle cell not contacted with the test compound.

In a seventh aspect, provided herein are methods for identifying a compound that is an antagonist of a bitter taste receptor, comprising contacting an airway cell that naturally expresses a bitter taste receptor with a test compound and with a bitter tastant, and measuring activity of the bitter taste receptor, wherein a test compound that inhibits activity of the bitter taste receptor compared to the activity of the bitter taste receptor in a cell contacted with the bitter tastant but not contacted with the test compound, identifies an antagonist of the bitter taste receptor. For example, the activity of the bitter taste receptor is measured by measuring a change in intracellular calcium release or a change in intracellular IP3. The test compound can be added before, after, or simultaneously with the bitter tastant.

In the screening methods described herein, the airway cell can be an airway smooth muscle cell or a non-ciliated airway epithelial cell.

Studies were performed with cultured primary ASM cells loaded with Fluo-4 AM. (a, b) $[Ca^{2+}]_i$ transients and dose response curves to saccharin and chloroquine from 5-6 experiments. (c) Maximal $[Ca^{2+}]_i$ responses to 1.0 mM of the bitter tastants aristocholic acid, chloroquine, colchicine, denatonium, quinine, saccharin, salicin, strychnine and yohimbine, the bronchoconstrictive $G_q$-coupled agonists histamine (0.1 mM) and bradykinin (0.01 mM), and 1.0 mM of the sweet tastants sucralrose and SC45647. Results are from 4-6 experiments. *, $P<0.01$ vs. basal; #, $P<0.05$ vs. denatonium. (d) The $[Ca^{2+}]_i$ response is ablated by the PLC inhibitor U73122 and the βγ antagonist gallein, and attenuated by the $IP_3$ receptor antagonist 2APB. These studies were performed in the absence of extracellular calcium. Results shown are from a single representative experiment of at least 3 performed.

Figure 2:
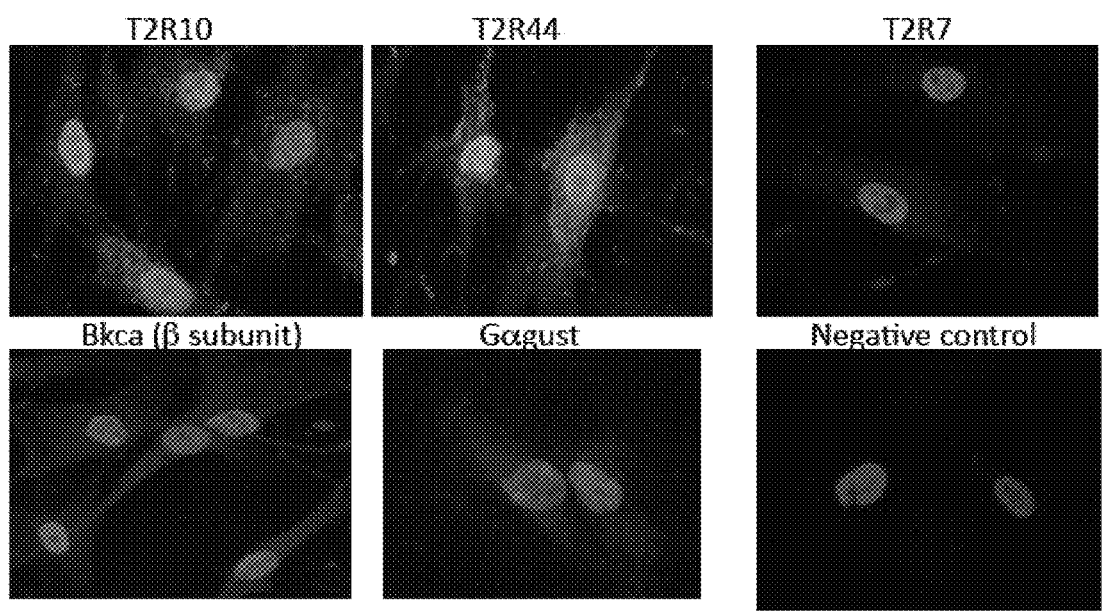

FIG. 2—Expression of bitter taste receptor and other proteins on human airway smooth muscle cells by immunocytochemistry. Sections of cells were processed by a standard method as described elsewhere[31], and antisera were utilized to identify the indicated proteins. The antisera was directed against T2Rs 10, 44, and 7, gustducin and $BK_{Ca}$. Protein expression of T2R10 and T2R44, whose mRNAs were found in high abundance by RT-PCR (see Table 2) were detected on human ASM as red signals, whereas T2R7 whose mRNA was not detected, showed no signal. The negative control in the second row represents background signal in the absence of antisera. Nuclei were identified by the blue color from DAPI fluorescence. Gustducin and $BK_{Ca}$ proteins were also identified as shown. (Results are representative of 3 experiments, with >100 cells imaged per experiment, magnification 60×.)

Figure 3:
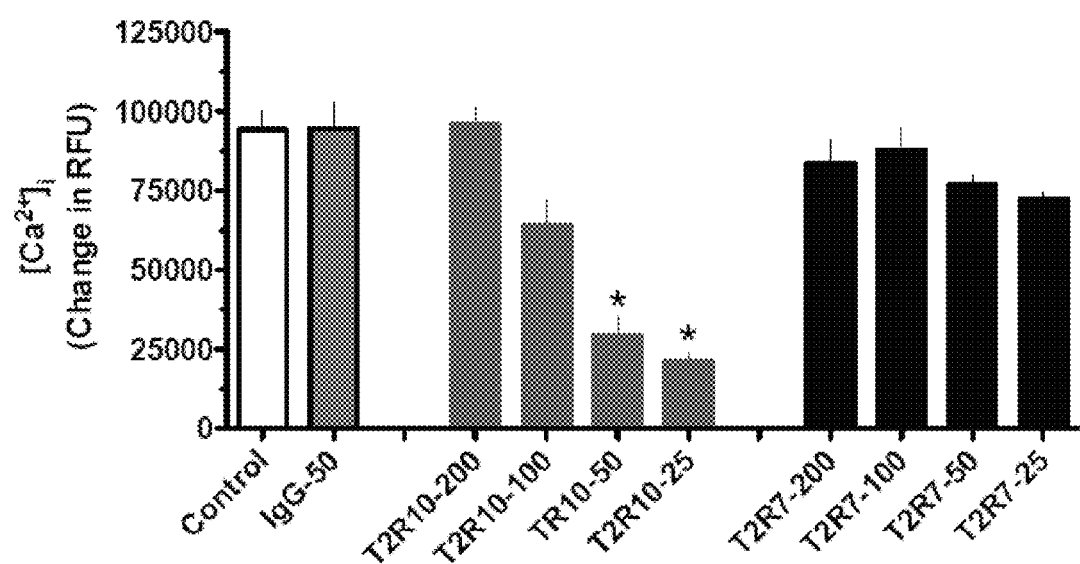

FIG. 3—T2R10 blockade by incubation of ASM cells with polyclonal T2R10 antisera inhibits strychnine-promoted $[Ca^{2+}]_i$ increases. Cells were incubated for 2 hours with the indicated titers (1:200 to 1:25) of T2R10 and T2R7 antisera, a 1:50 titer of isotype-specific IgG, or media alone (control). $[Ca^{2+}]_i$ was stimulated by the T2R10 agonist strychnine (1 mM). T2R10 antisera decreased strychnine-promoted $[Ca^{2+}]_i$ increases. Neither IgG or antisera to T2R7 (which is not expressed in ASM) had a significant effect on $[Ca^{2+}]_i$ stimulation. *, $P<0.01$ vs. control.

Figure 4:
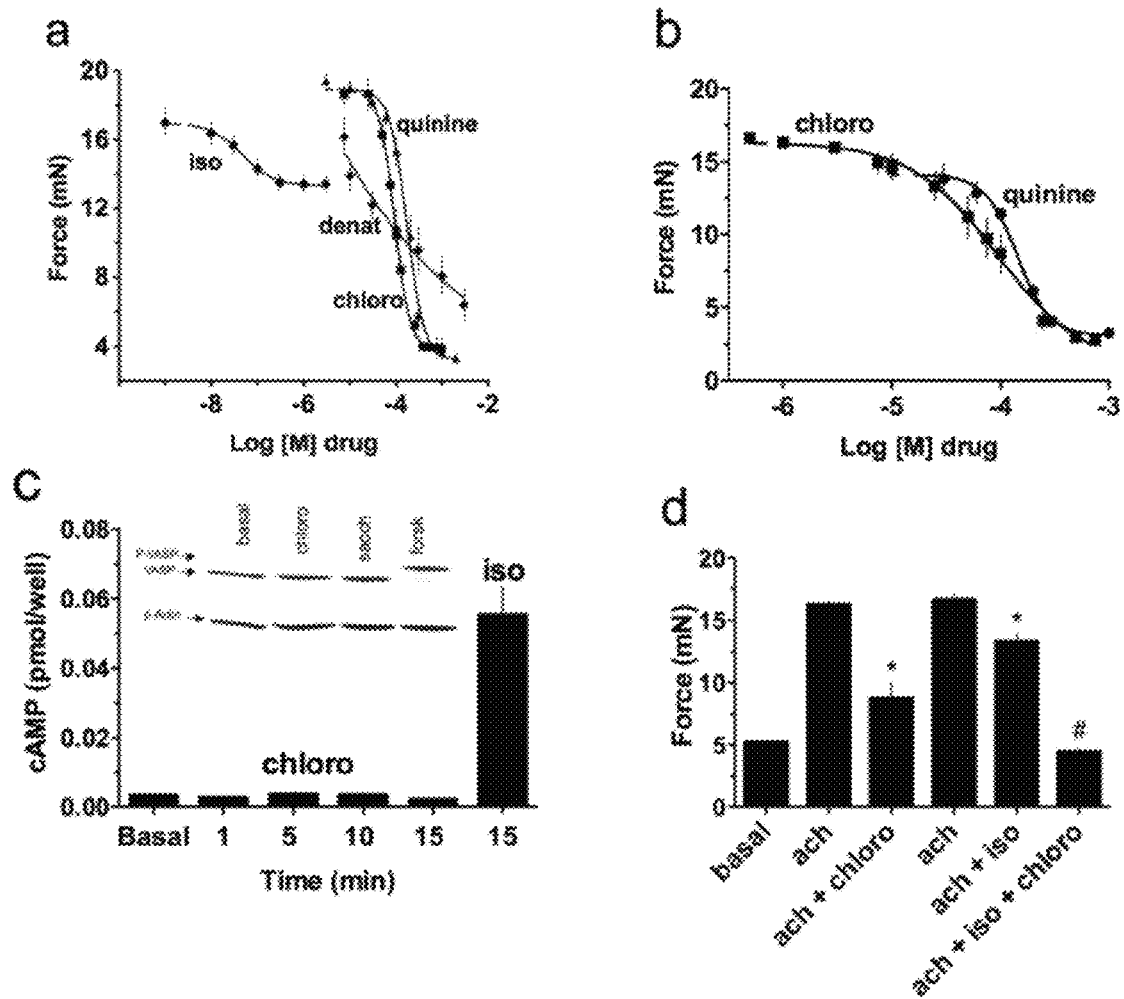

FIG. 4—Bitter tastants evoke bronchodilatation in a non-cAMP dependent manner. (a) Dose-response curves of relaxation for the β-agonist isoproterenol (iso) and the bitter taste receptor agonists chloroquine (chloro), denatonium (denat), and quinine, derived from intact mouse tracheas contracted with 1.0 mM acetylcholine (n=7 experiments). (b) Chloroquine and quinine relax intact mouse airway tracheas contracted by 1.0 mM serotonin (n=4 experiments). (c) Cultured human ASM cells were incubated with 1.0 mM chloroquine for the indicated times, or for 15 min with 30 μM isoproterenol, and cAMP measured by radioimmunoassay. There was no evidence for chloroquine-promoted cAMP accumulation (n=3 experiments). Inset: Cultured human ASM cells were exposed to 1.0 mM chloroquine or saccharin (sacc), or 10 μM forskolin (forsk), and cell extracts were immunoblotted to ascertain PKA-mediated VASP phosphorylation (upper band), a cAMP promoted event. Forskolin, which stimulates cAMP production, resulted in phosphorylation of VASP as indicated by the upper band. Neither chloroquine nor saccharin promoted VASP phosphorylation, consistent with the cAMP measurements. (d) The airway relaxation response to isoproterenol and chloroquine are additive. Intact mouse tracheas were contracted with 1.0 mM acetylcholine (ach) which was maintained in the bath when chloroquine (200 μM) or isoproterenol (30 μM), or both drugs, were added. After chloroquine exposure the rings were washed and then rechallenged with the same dose of acetylcholine. *, $P<0.05$ vs. acetylcholine alone; #, $P<0.01$ vs. acetylcholine+isoproterenol, or chloroquine alone. Results are from 4 experiments.

Figure 5:
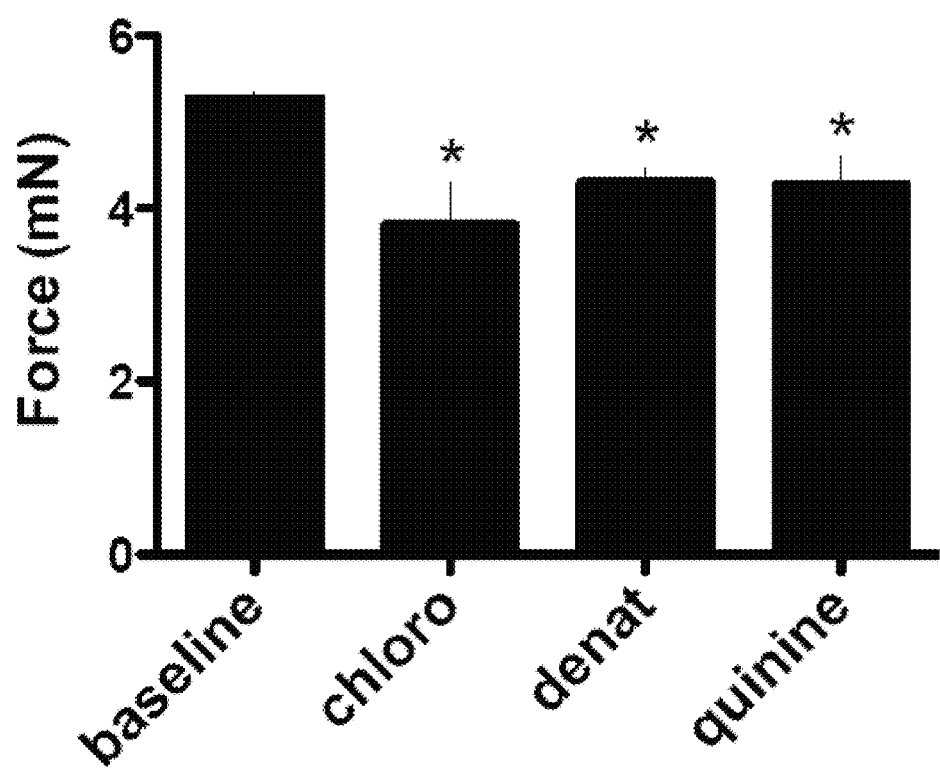

FIG. 5—Bitter tastants relax baseline airway tension. Mouse tracheal rings were placed at a passive tension of ~5 mN, and were exposed to 1.0 mM of chloroquine, denatonium, or quinine. Results are from 4 experiments. *, $P<0.05$ vs. baseline.

Figure 6:
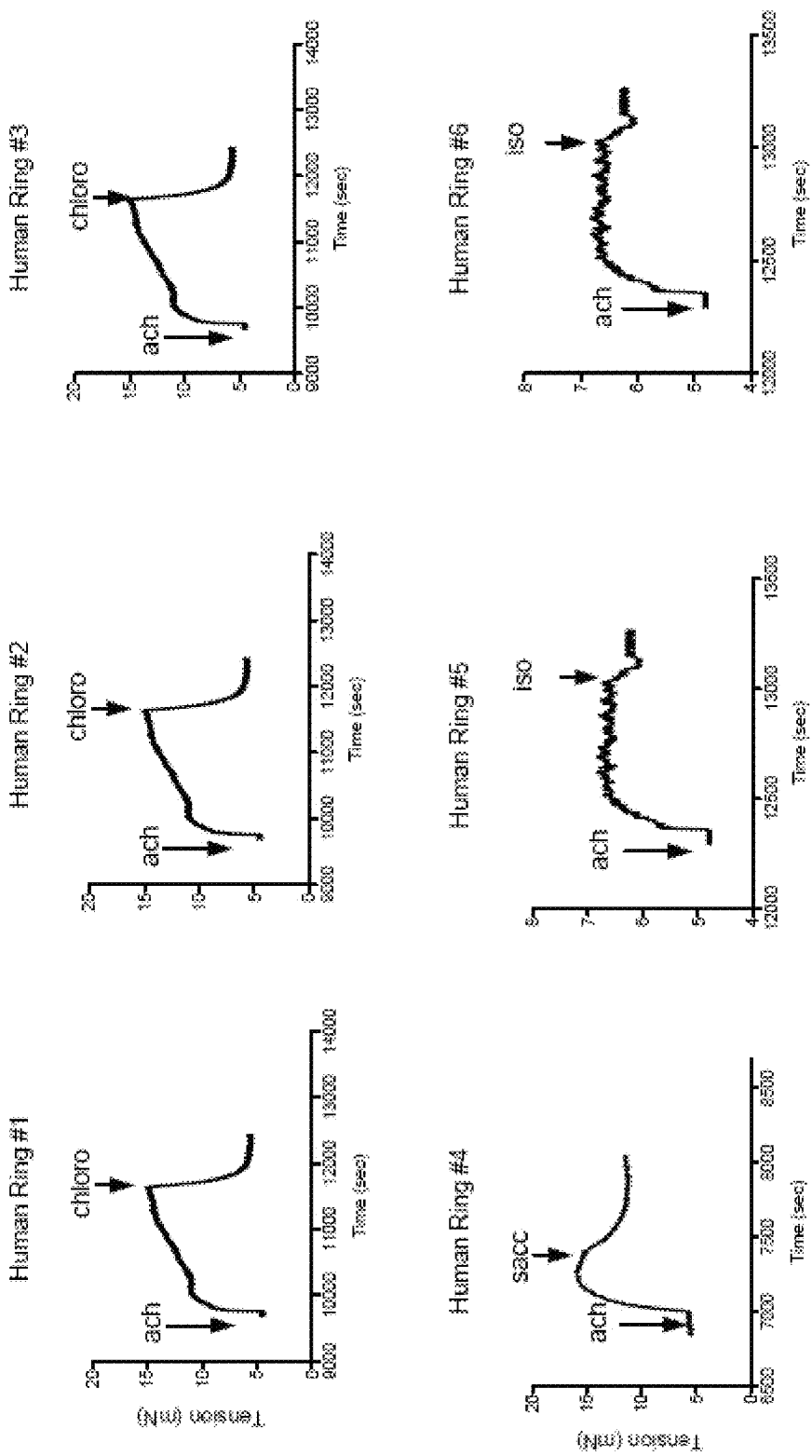

FIG. 6—Bitter tastants relax human airway smooth muscle. Rings from fourth generation bronchi from grossly normal lung tissue obtained from surgical specimens were mounted as described in the Examples. Rings were set to a passive tension of 5 mN, contracted continuously with 1.0 mM acetylcholine, and then exposed to 1 mM chloroquine or saccharin, or, 10 μM isoproterenol. Shown are the results from individual experiments performed with 6 rings from 3 individuals.

Figure 7:
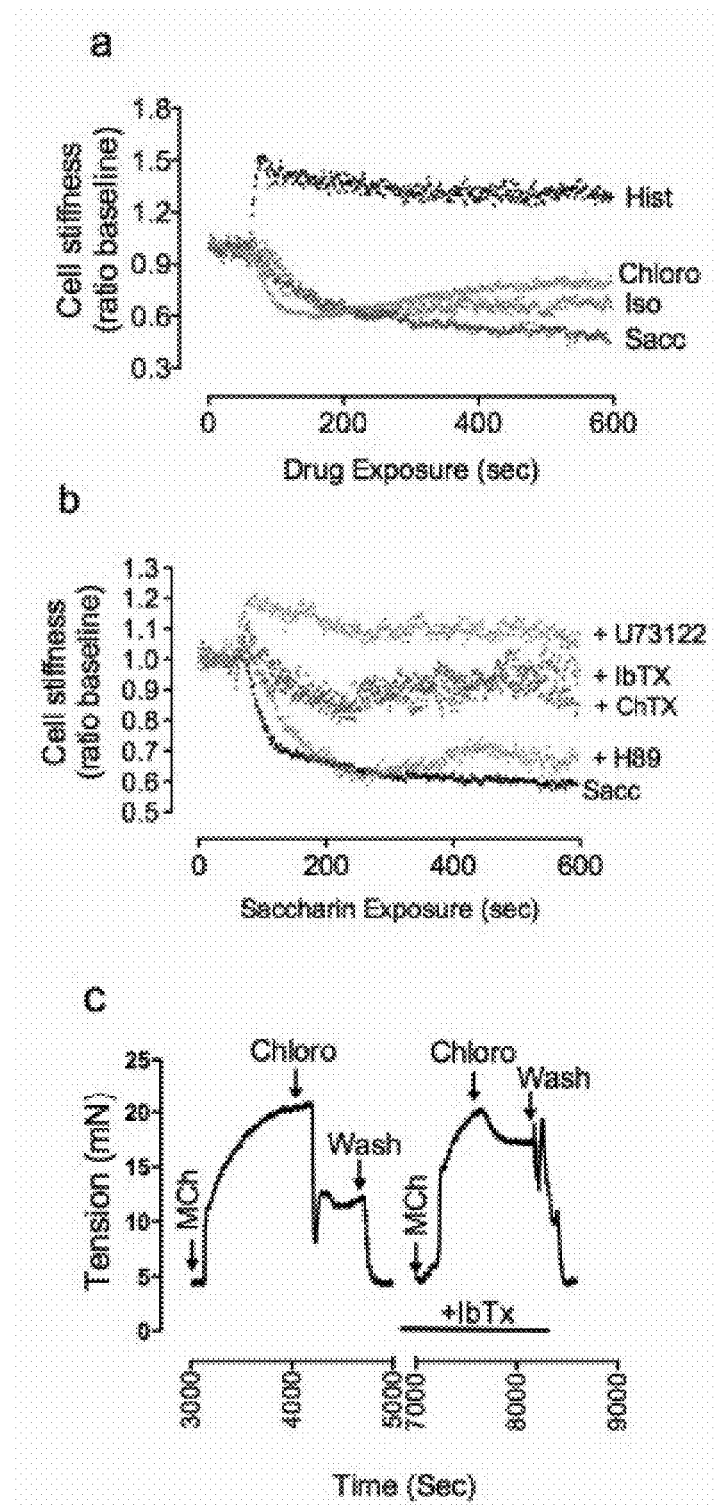

FIG. 7—Isolated airway smooth muscle responses to bitter tastants as assessed by single cell mechanics. (a) Isoproterenol (Iso), chloroquine (Chloro) and saccharin (Sacc) relax, while histamine (Hist) contracts, isolated ASM cells. (b) The relaxation responses in isolated ASM cells to 1 mM saccharin are inhibited by the PLCβ inhibitor U73122 (1 μM), 100 nM of the $BK_{Ca}$ antagonists iberiotoxin (IbTx) and charybdotoxin (ChTx), but are unaffected by 100 nM of the PKA inhibitor H89. (c) The relaxation response to 1 mM Chloro in isolated mouse airway is inhibited by 100 nM IbTx. Results are representative of 5-8 experiments performed.

Figure 8:
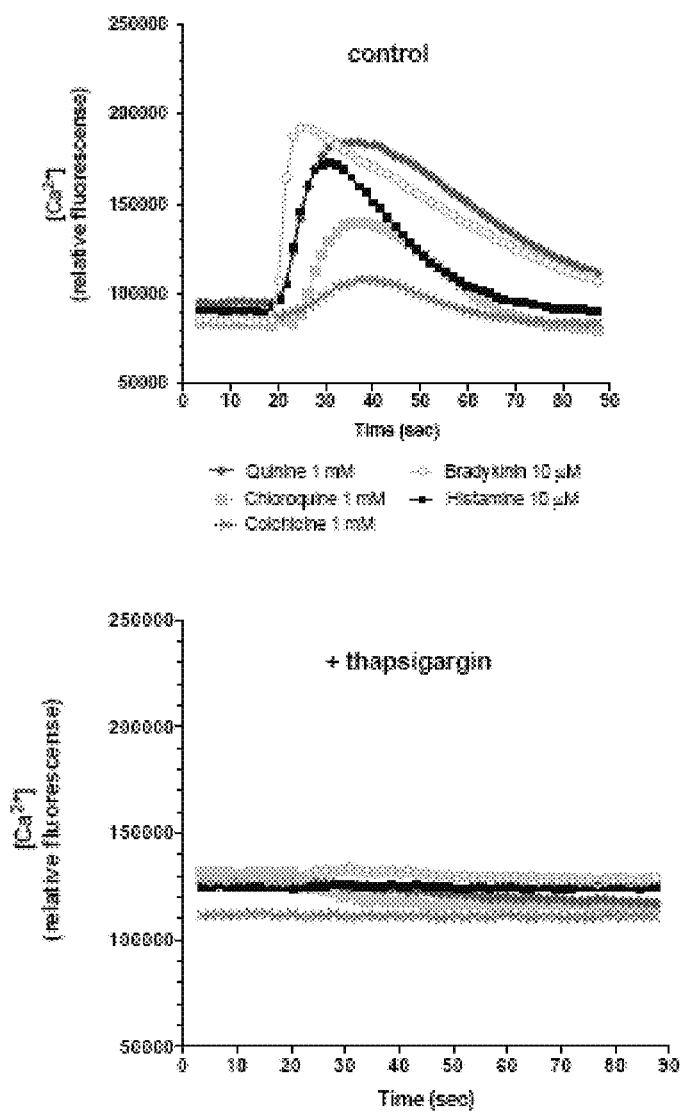

FIG. 8—Depletion of SR calcium by thapsigargin ablates bitter tastant stimulation of $[Ca^{2+}]_i$ in human ASM cells. Cells were treated with carrier (control) or 10 μM thapsigargin for 30 min and bitter tastant-mediated $[Ca^{2+}]_i$ release measured as described in the Examples. The $G_q$-coupled receptor ligands bradykinin and histamine, which also stimulate increases in $[Ca^{2+}]_i$ derived from SR stores were utilized as controls. The $[Ca^{2+}]_i$ responses to all agonists were ablated by thapsigargin treatment. Shown are tracings from a single experiment, representative of 4 performed.

Figure 9:
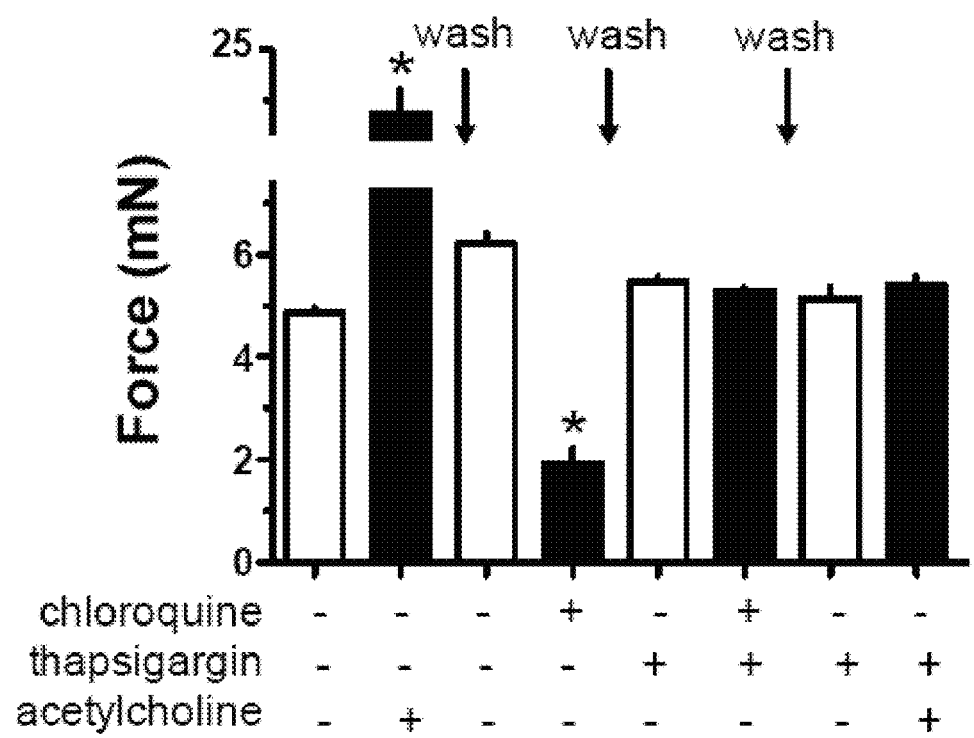

FIG. 9—Depletion of SR calcium by thapsigargin ablates chloroquine-mediated relaxation of intact mouse tracheal rings. Rings were placed at a passive tension of ~5 mN, and exposed to carrier, chloroquine (3.0 mM), or acetylcholine (1.0 mM) as indicated without and with preincubation with 10 μM thapsigargin. Each white bar indicates a baseline tension after a wash and in the absence or presence of thapsigargin. Results are from 4 experiments. *, $P<0.01$ vs. the paired baseline tension.

Figure 10:
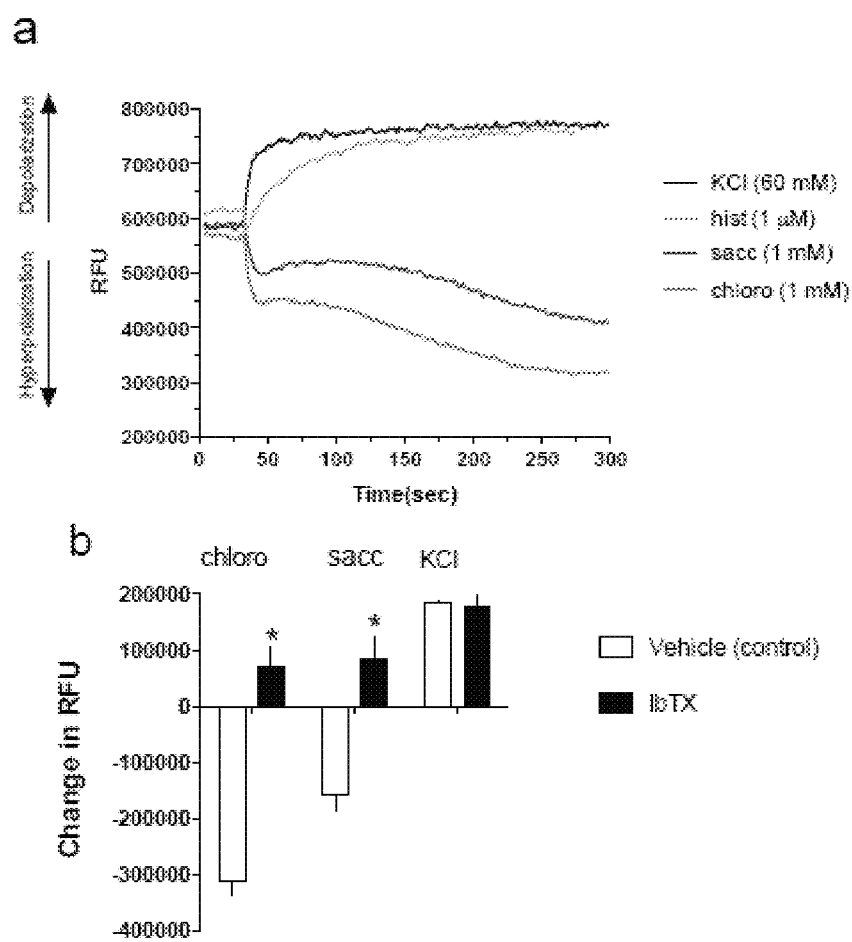

FIG. 10—Bitter tastants evoke membrane hyperpolarization in ASM cells which is sensitive to iberiotoxin. Cells were loaded with a fluorescence-based membrane potential-sensitive dye as described[19] and data acquired after addition of the indicated agents as described in the Examples (top trace=KCl; below top trace=hist; bottom trace=chloro; above bottom trace=sacc). An increase in fluorescence indicates depolarization while a decrease indicates hyperpolarization. a) Exposure to 60 mM KCl and 1.0 μM histamine resulted in the expected depolarization. The bitter tastants saccharin and chloroquine (1 mM) evoked hyperpolarization. Results are from a single experiment representative of 4 performed. b) Preincubation with 100 nM of the specific $BK_{Ca}$-channel antagonist iberiotoxin (IbTX) inhibited membrane hyperpolarization from both bitter tastants. Results represent the peak responses from 4 experiments. *, P<0.01 vs. vehicle control.

Figure 11:
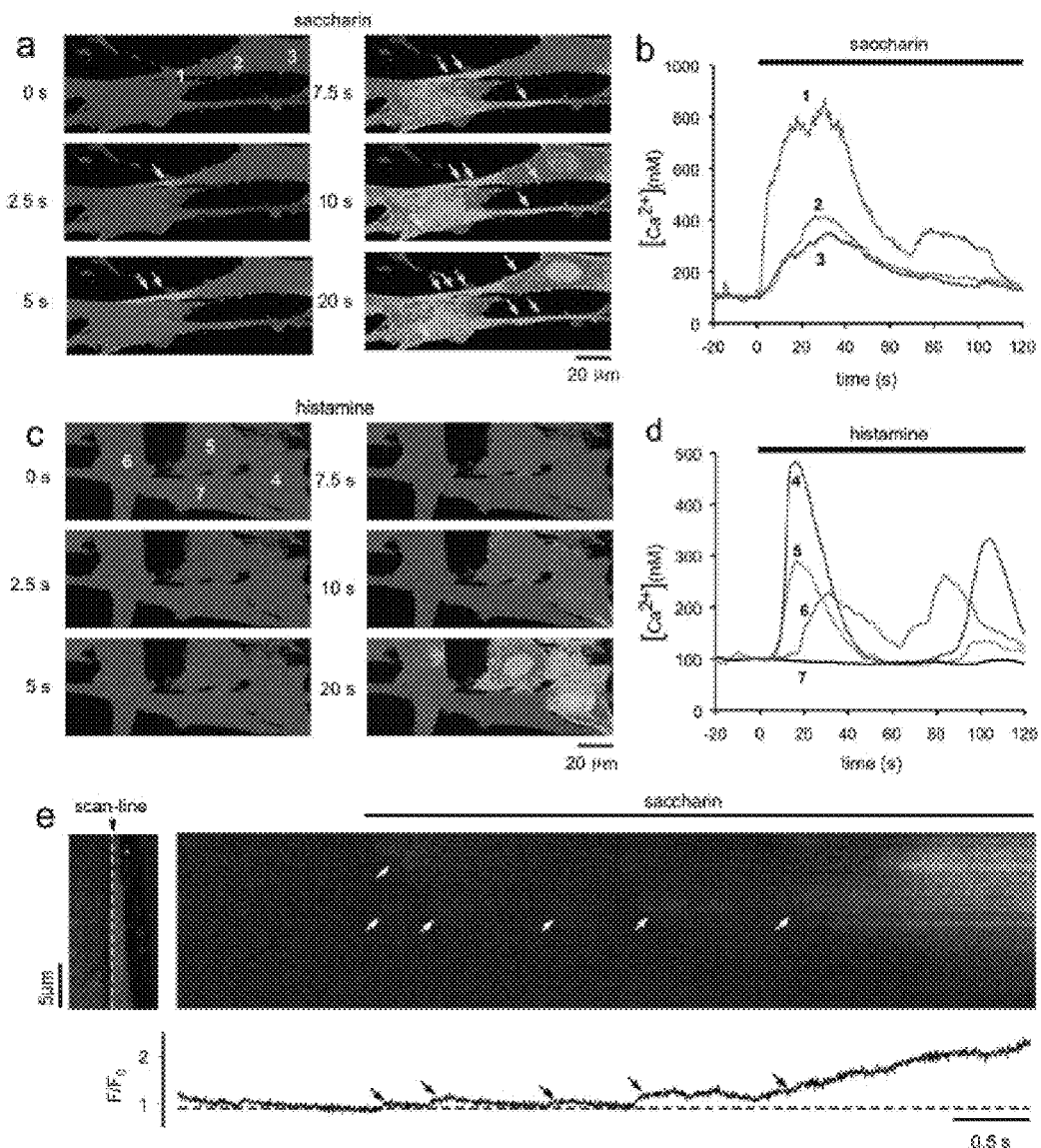

FIG. 11—Saccharin preferentially triggers localized $[Ca^{2+}]_i$ responses in ASM cells. (a,c) Sequential confocal images of Fluo-3 loaded cells shows activation of localized $[Ca^{2+}]_i$ increases in the cell periphery upon exposure of ASM cells to 0.3 mM saccharin, and a generalized increase in $[Ca^{2+}]_i$ with exposure to 1.0 µM histamine. The images are Fluo-3 fluorescence after background subtraction and baseline normalized (F/F$_0$) with intensity encoded by pseudo-color. The arrows highlight local $[Ca^{2+}]_i$ "hot-spots". (b,d) Local $[Ca^{2+}]_i$ transients measured in regions of interest (ROI). Saccharin activated a rapid rise of $Ca^{2+}$ in the peripheral end (ROI 1), but a smaller and gradual increase of $[Ca^{2+}]_i$ in the central regions (ROI 2,3) of the cell. The histamine response (ROI 4-7) was asynchronous and was observed throughout the cells. (e) Confocal linescan imaging shows spatially and temporally resolved local $[Ca^{2+}]_i$ events activated by saccharin in a peripheral site. The scan line (white dashed line) was placed within 1 µm parallel to the cell membrane at one end of an elongated ASM cell as shown in the left panel. Arrows indicate several local $[Ca^{2+}]_i$ events that occur prior to the more defined increase within the isolated region. The bottom panel is the spatially averaged normalized fluorescence signal (F/F$_0$) generated from the linescan. Results are from single experiments representative of five performed. See Methods for the number of data acquisitions utilized to construct images.

Figure 12:
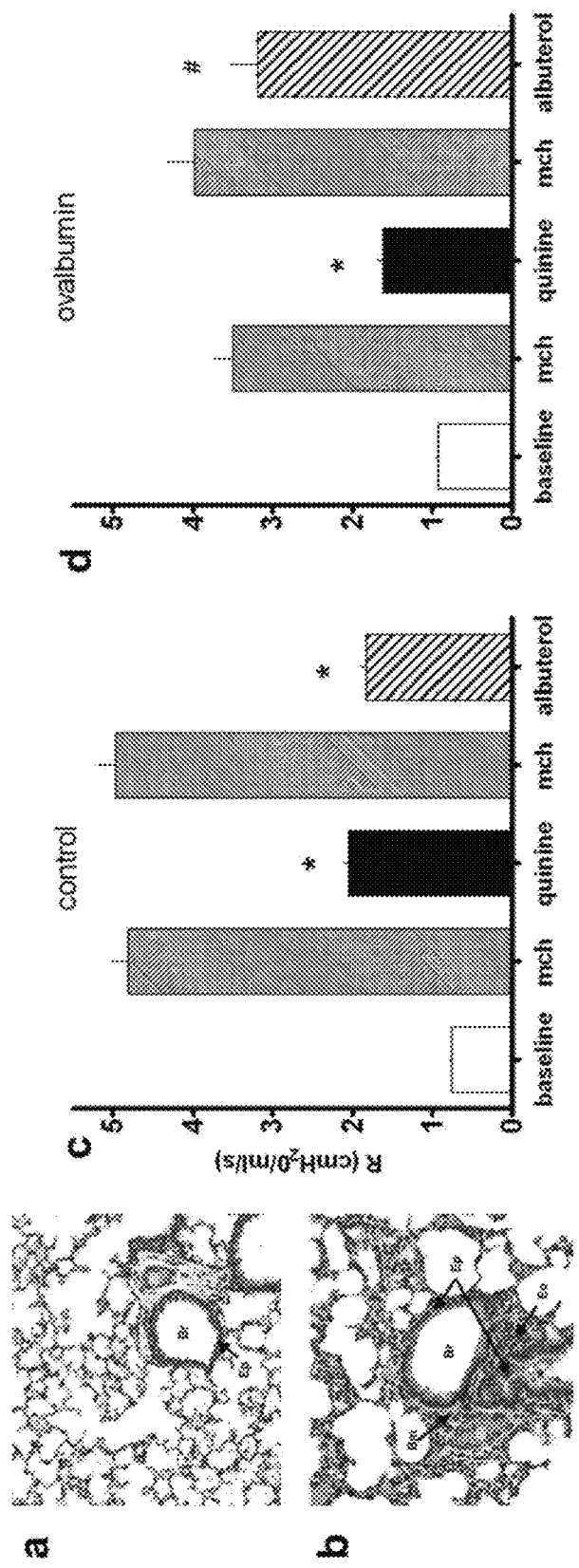

FIG. 12—Bitter taste receptor agonists relieve bronchoconstriction in a mouse model of asthma. (a,b) Photomicrographs from sections of control and ovalbumin challenged mouse lungs shows eosinophilic inflammation of the airway, epithelial hyperplasia and basement membrane thickening in ovalbumin challenged airways (hematoxylin and eosin stain, 40× magnification). Br, bronchus; Bm, basement membrane; Eo, eosinophil; Ep, epithelium; Bl, blood vessel. Airway resistance in control (c) and ovalbumin challenged mice (d) was measured at baseline, and in response to aerosolized methacholine (mch), and to quinine or the β-agonist albuterol given during the bronchoconstrictive phase (n=5 experiments). *, P<0.01 vs. methacholine; #, P<0.05 vs. methacholine.

Figure 13:
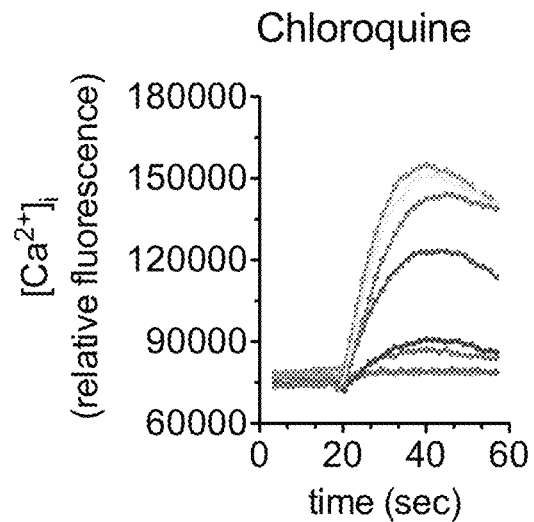

FIG. 13—$[Ca^{2+}]_i$ transients in human airway smooth muscle cells to various doses of the known bitter taste receptor agonist chloroquine using human airway smooth muscle cells.

Figure 14:
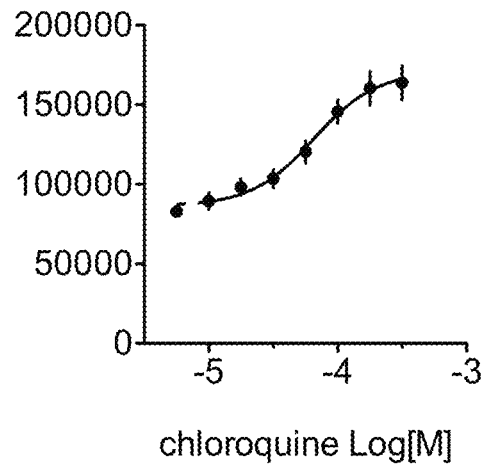

FIG. 14—Dose-response curve for chloroquine, a known bitter taste receptor agonist, using human airway smooth muscle cells. The potency was calculated as 70 micromolar. The efficacy was calculated as the net change in fluorescence units of 84,317.

Figure 15:
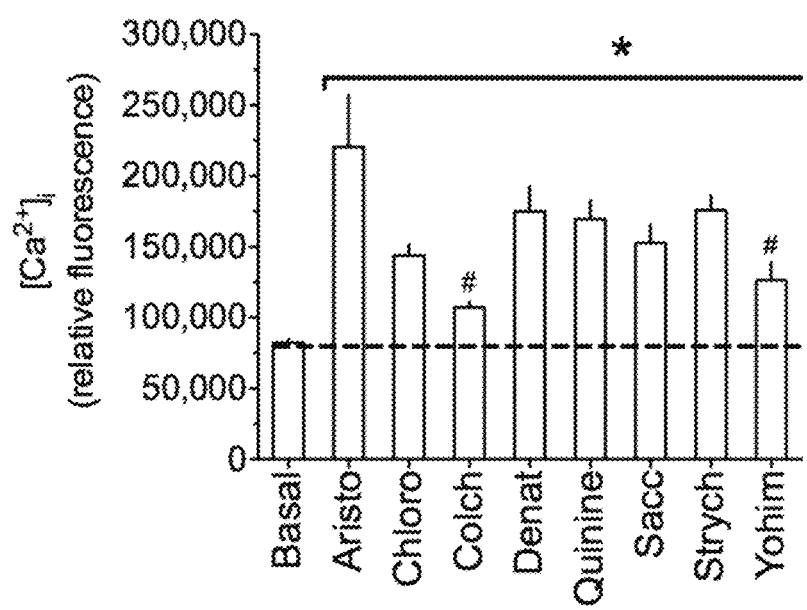

FIG. 15—Screening bitter taste receptor agonists for stimulating $[Ca^{2+}]_i$ in human airway smooth muscle cells using a fixed concentration (1 mM) of each compound.

Figure 16:
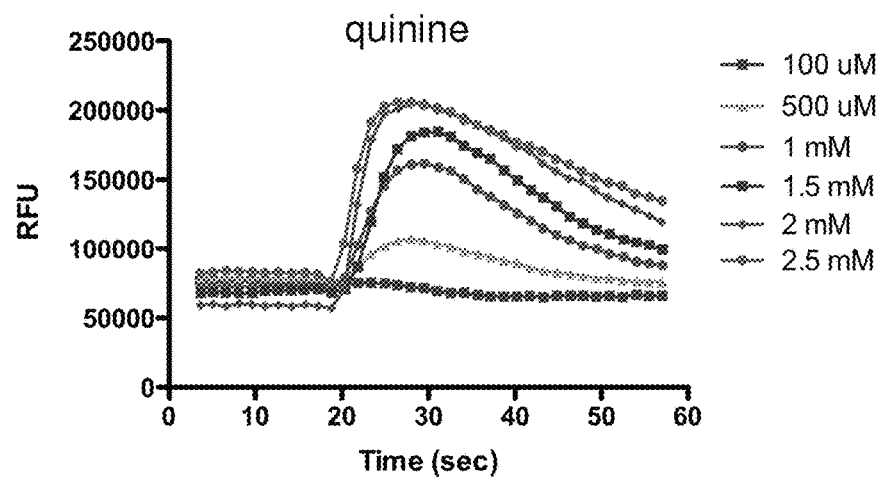

FIG. 16—$[Ca^{2+}]_i$ transients in H292 cells to various doses of the known bitter taste receptor agonist quinine. The doses of quinine are shown in reverse order from the legend, that is, the lowest trace at 50 seconds is 100 mU, while the next trace above is 500 uM, as so forth to the top trace at 50 seconds which is 2.5 mM.

Figure 17:
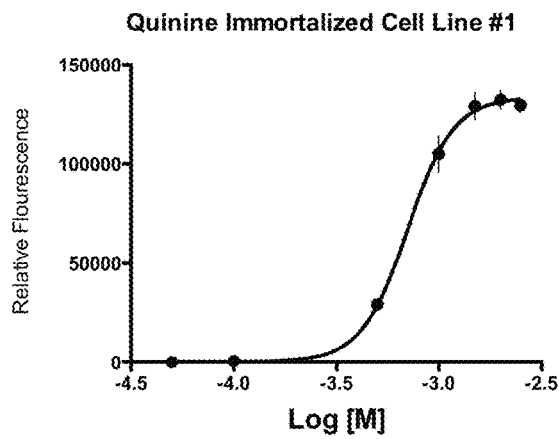

FIG. 17—$[Ca^{2+}]_i$-stimulated dose-response curve for quinine, a known bitter taste receptor agonist, using H292 cells. The potency was calculated 703 micromolar and the efficacy as 133,201 fluorescence units.

Figure 18:
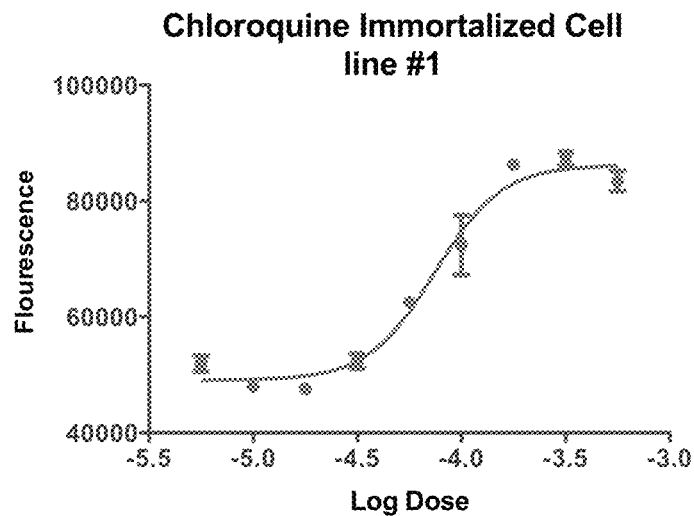

FIG. 18—$[Ca^{2+}]_i$-stimulated dose-response curve for chloroquine, a known bitter taste receptor agonist, using H292 cells. The potency was calculated as 74 micromolar, and the efficacy as 37,136 fluorescence units.

Figure 19:
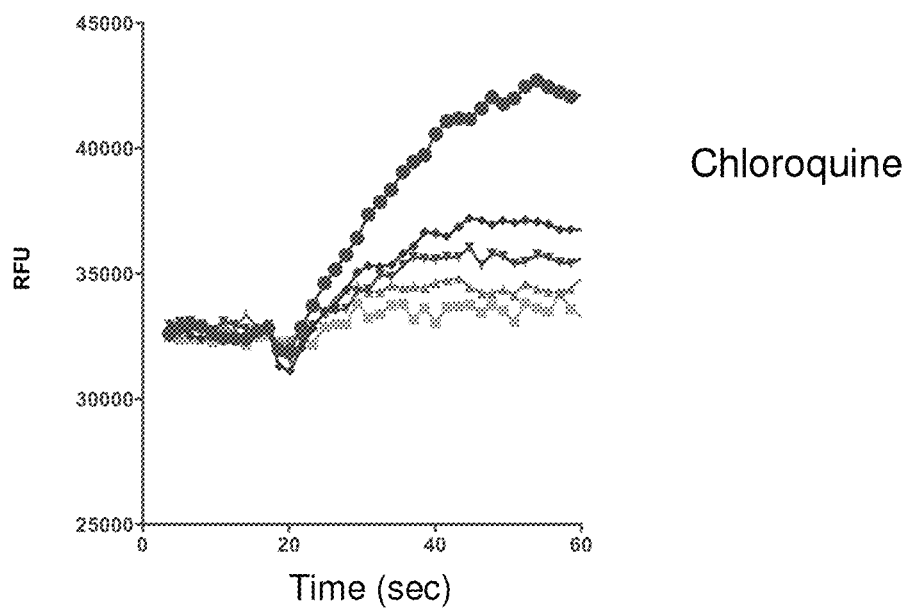

FIG. 19—$[Ca^{2+}]_i$ transients in BEAS2B cells to various doses of the known bitter taste receptor agonist chloroquine.

Figure 20:
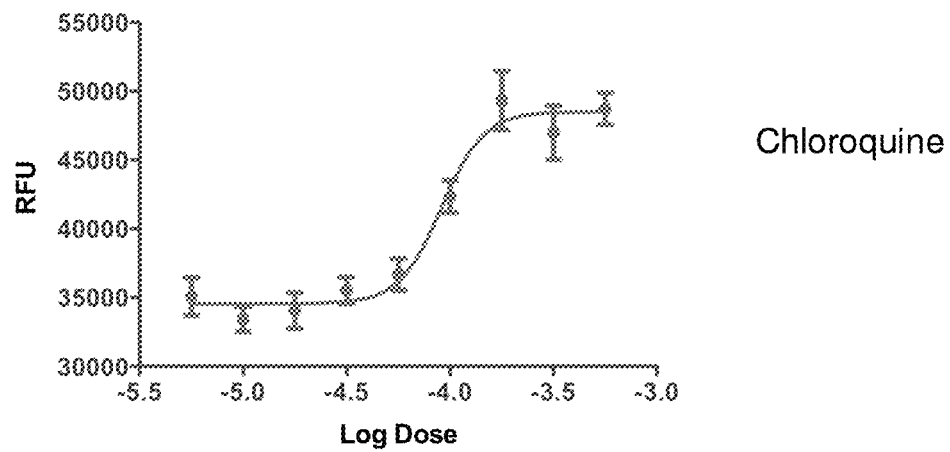

FIG. 20—$[Ca^{2+}]_i$-stimulated dose-response curve for chloroquine, a known bitter taste receptor agonist, using BEAS2B cells. The potency was calculated as 90 micromolar, and the efficacy as 13,995 fluorescence units.

DETAILED DESCRIPTION

Provided herein are novel methods for increasing airway dilation, e.g., for treating obstructive lung diseases such as asthma and COPD. The present treatment methods are based on the unexpected discovery that bitter taste receptors are expressed in isolated human airway smooth muscle (ASM). Receptors for bitter tastes on the tongue are thought to have evolved for avoidance of plant-based toxins[9,10]. These receptors are G-protein coupled receptors (GPCRs) and consist of at least 25 receptor subtypes, with each recognizing a repertoire of agonists that usually overlaps with other bitter taste receptors, creating a redundant, broadly-tuned, avoidance and rejection network[9,11-13]. The finding of bitter taste receptors on ASM led the present inventors to initially hypothesize that certain bronchospastic disorders, such as occupational asthma[14], might be caused by environmental inhalants acting at these airway receptors leading to contraction and bronchoconstriction. This notion was based on the fact that bitter taste receptors couple to increases in $[Ca^{2+}]_i$ in specialized taste cells of the tongue, and this signal is also found with known bronchoconstrictive GPCRs such as those for histamine, acetylcholine and bradykinin in ASM cells[2]. Using various approaches as disclosed herein, it was found that bitter tastants also increase $[Ca^{2+}]_i$ in ASM cells. However, paradoxically, the inventors discovered that bitter taste receptor agonists are bronchodilators, with significantly greater efficacy than any known therapeutic agent. These receptors transduce this relaxation response in ASM by a novel mechanism involving receptor generated Gβγ activation of phospholipase C(PLC) and a partitioned $[Ca^{2+}]_i$ transient that opens cell surface K$^+$ channels resulting in membrane hyperpolarization. These findings, discussed in detail in the Examples below, are the basis for the invention claimed herein.

In various aspects of the invention, methods of treatment are provided that are based on the novel finding that bitter tastants induce relaxation of airway smooth muscles and bronchodilation, and that administration of bitter tastants to a subject can be used to treat conditions and diseases associated with bronchoconstriction. Thus, in one aspect the present invention provides methods of treating an obstructive lung disease or condition in a subject, comprising administering a therapeutically effective amount of a pharmaceutical composition comprising a bitter tastant to a subject in need of treatment. In a second aspect the present invention provides methods of inducing bronchodilation in a subject, comprising administering a therapeutically effective amount of a pharmaceutical composition comprising a bitter tastant to a subject in need of bronchodilation. In a third aspect the present invention provides methods of relaxing airway smooth muscle (ASM) in a subject, comprising administering a therapeutically effective amount of a pharmaceutical composition comprising a bitter tastant to a subject in need of ASM relaxation. In a fourth aspect the present invention provides methods of treating or preventing bronchoconstriction or bronchospasm in a subject, comprising administering a therapeutically effective amount of a pharmaceutical composition comprising a bitter tastant to a subject in need of treatment or prevention of bronchoconstriction or bronchospasm. In a related aspect, the present invention provides methods for identifying a compound for relaxing airway smooth muscle, comprising contacting an airway smooth muscle cell with a test compound that binds to a bitter tastant receptor and determining whether the test compound relaxes the airway smooth muscle cell, wherein a compound that relaxes the smooth muscle cell is identified as a compound for relaxing airway smooth muscle.

In each of the above aspects of the invention, the identity of the bitter tastant (BT) is not critical to the success of the method, although it is envisioned that certain BTs will be more effective in particular methods, and in the treatment of particular conditions and diseases, than other BTs. There are many known synthetic agents which activate bitter taste receptors[10] that are non-toxic. And there are many plant-derived bitter tastants and their metabolites[10] that can have favorable therapeutic profiles. By "bitter taste receptor," "bitter tastant receptor," and the like is meant a T2R or TAS2R receptor as is known in the art and/or as described, e.g., in Chandrashekar et al., *Cell* 100:703-711 (2000); Adler et al., *Cell* 100:693-702 (2000); Chandrashekar et al. *Nature* 444:288-294 (2006); or Contea et al., *Cytogenet. Genome Res.* 98:45-53 (2002). By "bitter tastant" is meant any compound, whether synthetic or naturally-occurring, that binds to a bitter tastant receptor present on the surface of an airway smooth muscle cell and, via such binding, relaxes the airway smooth muscle cell; any such compound is considered to be a bitter tastant for use in the methods described herein. Examples of bitter tastants that can be used in the pharmaceutical compositions and methods of the present invention include, and are not limited to, one or more of the following: aristocholic acid, chloroquine, colchicine, denatonium, quinine, saccharin, salicin, strychnine and yohimbine.

Such bitter tastants are "agonists" of one or more bitter taste receptors, and binding of such such agonists to their cognate bitter taste receptors can be detected by well-known methods, as described herein. Bitter taste receptor "antagonists" inhibit the binding of agonists to bitter taste receptors and/or otherwise inhibit the biochemical signaling cascade that is initiated by the binding of bitter taste receptor agonists to their cognate receptors. The decrease in binding and/or inhibition of bitter taste receptor signaling can be partial or complete. Accordingly, bitter taste antagonists can partially or fully decrease or mask bitter tastes in foodstuffs, pharmaceutical products, and other orally ingested products.

The obstructive lung diseases and conditions encompassed by the present invention include any respiratory condition or disease, whether acute or chronic, characterized by impairment of airflow into and/or out of the lungs of a subject. Obstructive lung diseases and conditions include, e.g., asthma, chronic obstructive pulmonary disease (COPD), emphysema and bronchitis, as well as cystic fibrosis, bronchiectasis, bronchiolitis, and allergic bronchopulmonary aspergillosis. Another such obstructive lung disease or condition that can be treated or prevented by administering bitter tastants as described herein includes bronchoconstriction or bronchospasm that can be caused, e.g., by inhalation of a noxious compound such as smoke or a corrosive chemical; by a respiratory infection; or by anaphylaxis such as that caused by sepsis or an allergic reaction to a food (e.g., peanuts), a drug (e.g., penicillin), an insect sting or bite, pollen, mold, dust mites, latex, or other substances; or by other triggers of bronchoconstriction or bronchospasm. For example, bitter tastants can be administered to prevent (or treat) bronchospasm induced by exercise or air pollution. In another example, bitter tastants can be administered before or during placement of a breathing tube to prevent (or treat) bronchospasm induced by placement of the tube. The bitter tastants of the invention can be administered to healthy individuals in situations in which it might be desirable to increase bronchodilation to improve oxygen uptake, e.g., in lower oxygen environments (such as several thousand feet above sea level) or to improve athletic performance.

In each of the embodiments of the present invention, the subject receiving treatment is a human or non-human animal, e.g., a non-human primate, bird, horse, cow, goat, sheep, a companion animal, such as a dog, cat or rodent, or other mammal. In some embodiments, the subject is a human.

The pharmaceutical compositions of the present invention comprising a bitter tastant may also comprise one or more of a carrier, diluent and excipient (e.g., a pharmaceutically acceptable carrier, diluent, or excipient), depending on the identity of the bitter tastant. By "pharmaceutically acceptable" is meant a material that is not biologically or otherwise undesirable, i.e., the material may be administered to an individual along with a bitter tastant without causing any undesirable biological effects or interacting in a deleterious manner with any of the components of the pharmaceutical composition in which it is contained. Conventional pharmaceutical practice may be employed to provide suitable formulations or compositions to administer such compositions to subjects. The terms specifically exclude cell culture medium. Suitable diluents (for both dry and liquid pharmaceutical formulations) are well known to those skilled in the art and include saline, buffered saline, dextrose (e.g., 5% dextrose in water), water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin; see, e.g., U.S. patent application publication 20060194717).

Carriers are compounds and substances that improve and/or prolong the delivery of an active ingredient to a subject in the context of a pharmaceutical formulation. Carrier may serve to prolong the in vivo activity of a drug or slow the release of the drug in a subject, using controlled-release technologies. Carriers may also decrease drug metabolism in a subject and/or reduce the toxicity of the drug. Carrier can also be used to target the delivery of the drug to particular cells or tissues in a subject. Common carriers (both hydrophilic and hydrophobic carriers) include fat emulsions, lipids, PEGylated phospholids, liposomes and liposheres, microspheres (including those made of biodegradable polymers or albumin), polymer matrices, biocompatible polymers, protein-DNA complexes, protein conjugates, erythrocytes, vesicles and particles.

Excipients included in a pharmaceutical composition have different purposes depending, for example on the nature of the drug, and the mode of administration. Examples of generally used excipients include, without limitation: stabilizing agents, solubilizing agents and surfactants, buffers and preservatives, tonicity agents, bulking agents, lubricating agents (such as talc or silica, and fats, such as vegetable stearin, magnesium stearate or stearic acid), emulsifiers, suspending or viscosity agents, inert diluents, fillers (such as cellulose, dibasic calcium phosphate, vegetable fats and oils, lactose, sucrose, glucose, mannitol, sorbitol, calcium carbonate, and magnesium stearate), disintegrating agents (such as crosslinked polyvinyl pyrrolidone, sodium starch glycolate, cross-linked sodium carboxymethyl cellulose), binding agents (such as starches, gelatin, cellulose, methyl cellulose or modified cellulose such as microcrystalline cellulose, hydroxypropyl cellulose, sugars such as sucrose and lactose, or sugar alcohols such as xylitol, sorbitol or maltitol, polyvinylpyrrolidone and polyethylene glycol), wetting agents, antibacterials, chelating agents, coatings (such as a cellulose film coating, synthetic polymers, shellac, corn protein zein or other polysaccharides, and gelatin), preservatives (including vitamin A, vitamin E, vitamin C, retinyl palmitate, and selenium, cysteine, methionine, citric acid and sodium citrate, and synthetic preservatives, including methyl paraben and propyl paraben), sweeteners, perfuming agents, flavoring agents, coloring agents, administration aids, and combinations thereof.

The pharmaceutical compositions of the present invention can be formulated for pulmonary administration, whether for nasal or buccal inhalation. The unit dosage of the pharmaceutical composition may be conveniently delivered in the form of an aerosol spray from a pressurized pack or a nebulizer, or via a vaporizer. The pharmaceutical compositions may also be delivered as a formulated powder and the powder composition may be inhaled with the aid of an insufflation powder inhaler device. One example of a delivery system for inhalation is a metered dose inhalation (MDI) aerosol, which may be formulated as a dry suspension or wet solution of a pharmaceutical composition of the invention in a suitable propellant, such as a fluorocarbon or a hydrocarbon, including HFA-134a (1,1,1,2-tetrafluoroethane). The propellant may also include one or more stabilizing excipients, such as ethanol and oleic acid. In addition, any other appropriate route for administration can be employed, for example, but not limited to, intravenous, parenteral, transbuccal, transdermal, transcutaneous, subcutaneous, intranasal, aerosol, or oral administration. Therapeutic formulations may be in the form of liquid solutions or suspensions; for example, for oral administration, formulations may be in the form of tablets or capsules; for intranasal formulations, in the form of powders, nasal drops, or aerosols; for transdermal formulations, in the form of creams or distributed onto patches to be applied to the skin.

Effective amounts of bitter tastants in a pharmaceutical formulation will vary depending on the bitter tastants being used and the condition or disease being treated, as well as factors such as age of the subject and other medications being taken. Effective dosages will typically be set by an attending physician as is well known in the art. However, the concentration of bitter tastants delivered to a subject in a unit dose will generally range from about 0.05 mg to about 100 mg, or a value within this range. Bitter tastants can be administered in combinations (e.g., two or more bitter tastants) and/or in combination with one or more non-bitter tastant compounds (e.g. but not limited to a beta-agonist such as albuterol). In one non-limiting example provided herein, the airway relaxation response to isoproterenol plus chloroquine is additive; thus, under some circumstances, it can be appropriate to administer this combination to a subject in need thereof.

As used herein, the terms "dose", "dosage", "unit dose", "unit dosage", "effective dose" and related terms refer to physically discrete units that contain a predetermined quantity of active ingredient (bitter tastant) calculated to produce a desired therapeutic effect (e.g., bronchodilation or relaxation of the airways). These terms are synonymous with the therapeutically effective amounts and amounts sufficient to achieve the stated goals of the methods disclosed herein.

As used herein, the terms "treat", "treating", and "treatment" have their ordinary and customary meanings, and include one or more of, ameliorating a symptom of an obstructive lung disease or condition in a subject, blocking or ameliorating a recurrence of a symptom of an obstructive lung disease or condition in a subject, decreasing in severity and/or frequency a symptom of an obstructive lung disease or condition in a subject. As used herein, "treatment" includes at least partially, and at least temporarily, relieving bronchoconstriction (or bronchospasm) or increasing bronchodilation, so that the patient or subject can breathe more easily. Treatment means ameliorating, blocking, reducing, decreasing or inhibiting by about 1% to about 100% versus a subject to which a pharmaceutical composition has not been administered. Preferably, the ameliorating, blocking, reducing, decreasing or inhibiting is about 100%, 99%, 98%, 97%, 96%, 95%, 90%, 80%, 70%, 60%, 50%, 40%, 30%, 20%, 10%, 5% or 1% versus a subject to which a pharmaceutical composition has not been administered.

As used herein, the terms "prevent", "preventing", and "prevention" have their ordinary and customary meanings, and include one or more of preventing a symptom of an obstructive lung disease or condition in a subject, blocking a recurrence of a symptom of an obstructive lung disease or condition in a subject, and decreasing in frequency a symptom of an obstructive lung disease or condition in a subject. As used herein, "prevention" includes at least partially, and at least temporarily, blocking bronchoconstriction (or bronchospasm) so that breathing is not inhibited in the patient or subject. The prevention may be protection of about 100%, 99%, 98%, 97%, 96%, 95%, 90%, 80%, 70%, 60%, 50%, 40%, 30%, 20%, 10%, 5% or 1% in the subject, versus a subject to which a pharmaceutical composition has not been administered. The prevention lasts at least about 1, 2, 3, 4, 5, 6, 7, 8, 9, 10, 11, 12, 13, 14, 15, 16, 17, 18, 19, 20, 21, 22, 23, or 24, or more, hours after administration of a pharmaceutical composition.

Provided herein are methods for relaxing airway smooth muscle by activating a bitter tastant receptor on the surface of a smooth muscle cell, thereby relaxing the airway smooth muscle. The bitter tastant receptor can be activated by contacting the receptor with a bitter tastant. Bitter tastant receptors that can be activated include, for example, T2R10; T2R14; T2R44; T2R5; T2R4; T2R48; T2R3; T2R49; T2R45; T2R50; T2R47; T2R9; T2R13; TAS2R55; TAS2R46; TAS2R1; TAS2R8. In any of the methods provided herein, one or more of the aforementioned bitter tastant receptors can be activated. The bitter tastants can be used to prevent or treat bronchospasm or bronchoconstriction caused by various stimuli or underlying diseases or conditions; to increase bronchodilation; and/or to treat various diseases and conditions in which it would be desirable to relax airway smooth muscle.

For example, the present invention provides methods of treating asthma in a subject, comprising administering a therapeutically effective amount of a pharmaceutical composition comprising a bitter tastant to a subject in need of treatment.

In another example, the present invention provides methods of treating COPD in a subject, comprising administering a therapeutically effective amount of a pharmaceutical composition comprising a bitter tastant to a subject in need of treatment.

In yet another example, the present invention provides methods of treating bronchitis in a subject, comprising administering a therapeutically effective amount of a pharmaceutical composition comprising a bitter tastant to a subject in need of treatment.

In each of these aspects, the pharmaceutical composition can be in the form of an inhalant or can be administered systemically by any well-known method (e.g., but not limited to, oral, intravenous, buccal, transdermal, etc.). In each of these aspects, the pharmaceutical composition is preferably in the form of an inhalant.

Also provided herein are methods for identifying compounds for relaxing airway smooth muscle, comprising contacting an airway smooth muscle cell with a test compound that binds to a bitter tastant receptor and determining whether the test compound relaxes the airway smooth muscle cell, wherein a compound that relaxes the smooth muscle cell is identified as a compound for relaxing airway smooth muscle. Bitter tastant receptors to which a test compound can bind include, for example, T2R10; T2R14; T2R44; T2R5; T2R4; T2R48; T2R3; T2R49; T2R45; T2R50; T2R47; T2R9; T2R13; TAS2R55; TAS2R46; TAS2R1; TAS2R8 (nomenclature as in Table 2; see Table 3 for alternative nomenclature). In any of the methods provided herein, the bitter tastant can bind to one or more of the aforementioned bitter tastant receptors.

Also provided herein are methods for identifying compounds that are bitter taste receptor agonists.

Also provided herein are methods for identifying compounds that are bitter taste receptor antagonists.

Identification of Bitter Taste Receptor Agonists and Antagonists

The inventors' discovery that bitter taste receptors are expressed on the surface of airway cells (such as airway smooth muscle cells and non-ciliated airway epithelial cells) provides new screening approaches for identifying compounds that serve as bitter taste receptor agonists and antagonists. Bitter taste receptor agonists can be used as described herein, e.g., to relax airway smooth muscle and for any other use in which it would be desirable to activate a bitter taste receptor. Bitter taste receptor antagonists find many uses, e.g., included as an ingredient to decrease or mask bitterness in foods and beverages; medications, neutraceuticals, and food supplements; oral care products; and the like. Candidate bitter taste receptor antagonists identified by the methods described herein can be further evaluated by well-known methods, e.g., by combining candidate bitter taste receptor antagonists with consumables or other orally-ingested products and subjecting the products to taste-testing by people who are sensitive to bitter taste perception.

Test compounds can be any synthetic or naturally occurring molecule. Compounds can be identified from libraries of compounds, e.g., but not limited to, combinatorial compound libraries or librariesof naturally-occurring compounds (e.g. but not limited to peptides, proteins, sugars, carbohydrates, nucleotides, nucleic acids, lipids, and/or derivatives or mixtures thereof), as is well known in the art. Test compounds can include compounds with known structural similarity to bitter taste receptor agonists or antagonists. The skilled artisan will appreciate that there are many commercial sources of synthetic and natural chemical compound libraries, e.g. but not limited to: TimTec USA, Princeton BioMolecular Research, Aurora Fine Chemicals, and the like. Numerous methods for preparing and screening combinatorial and other compound libraries is well-known in the art. See, e.g., U.S. Pat. No. 7,393,65; U.S. Patent Pub. 2010/0129833; and U.S. Patent Pub. 2010/0113548, each of which is herein incorporated by reference in its entirety.

Binding of a test compound (i.e., a potential agonist or antagonist) of a bitter taste receptor can be detected by any suitable approach. For example, binding of a bitter tastant to a bitter taste receptor initiates intracellular events such as an increase in inositol triphosphate (IP3) via a phospholipase C-mediated hydrolysis of phosphatidylinositol (PI). IP3 in turn stimulates the release of intracellular calcium stores. Accordingly, using well-known methods to detect such changes, changes in cytoplasmic calcium concentration or changes in second messenger levels can be used to identify bitter taste receptor agonists or antagonists. In addition to the methods described herein, see, e.g., U.S. Pat. No. 7,393,654; U.S. Patent Pub. 2010/0129833; and U.S. Patent Pub. 2010/0113548 (each of which is herein incorporated by reference in its entirety) for examples of such useful methods. "Measuring activity of the bitter taste receptor" means measuring a change in biochemical signaling effected by a bitter taste receptor (e.g., a change in intracellular calcium release, IP3 levels, or other signaling molecule levels) or measuring the amount of binding of a bitter tastant to a bitter tastant receptor. For example, an antagonist to a bitter taste receptor can be identified by its ability to inhibit binding of a known bitter tastant to its cognate receptor or to inhibit bitter tastant-mediated increases in biochemical signaling, e.g., as evidenced by intracellular calcium release, IP3 generation, and the like. Conversely, a bitter tastant receptor agonist is identified by its ability to bind to a bitter tastant receptor and/or to stimulate bitter tastant-mediated biochemical signaling as described herein and as is well-known in the art. For examples of such well-known assays to detect bitter tastant agonists and antagonists, see, e.g., U.S. Pat. No. 7,393,65; U.S. Patent Pub. 2010/0129833; and U.S. Patent Pub. 2010/0113548.

In addition, as described herein, bitter taste receptor agonists and antagonists can be identified by their ability to relax airway smooth muscle cells (in the case of a bitter taste receptor agonist) or to inhibit such relaxation (in the case of a bitter taste receptor antagonist). An at least 10% increase in bitter taste receptor-mediated activity identifies a bitter taste receptor agonist. An at least 10% decrease in agonist-mediated bitter taste receptor activity identifies a bitter taste receptor antagonist. Such changes can be, e.g., changes of at least 10%, 20%, 30%, 40%, 50%, 60%, 70%, 80%, 90%, 10%, etc.

In one example, cells are grown in multi-well dishes, loaded with a fluorescence-based calcium indicator dye, and test compounds are added with subsequent monitoring of the change in fluorescence indicative of a change in intracellular calcium $[Ca^{2+}]_i$ release. Test compounds can include, e.g., those with structural similarities to the known bitter taste receptor agonists or antagonists.

When cells are treated with a compound that serves as bitter taste receptor agonist, a dose-dependent rise in $[Ca^{2+}]_i$ is observed. From dose-response curves the potency (also known as the effective concentration where 50% of the maximal response occurs; EC50) and the efficacy (the maximal $[Ca^{2+}]_i$ response) can be ascertained for the compound.

Antagonists of bitter taste receptors are specifically identified as such by their ability to block agonist activation of $[Ca^{2+}]_i$ in these cells. Accordingly, binding of an antagonist to a bitter taste receptor would result in no change, or a decrease, in $[Ca^{2+}]_i$ when studied alone. Experiments to identify bitter taste receptor antagonists are performed by treating the cells with the proposed antagonist and a known agonist for a bitter taste receptor. Comparison of the $[Ca^{2+}]_i$ signal from the known agonist and the signal from that agonist in the presence of the proposed antagonist compound provides evidence that the test compound is acting to block access of the agonist to the receptor, which is indicative of an antagonist. The use of various doses of the proposed antagonist reveals the potency (defined above) and the efficacy (here defined as the maximal inhibition of the agonist signal).

A specific example is the use of the bitter taste receptor agonist acesulfame K at a fixed concentration of 800 micromolar with multiple concentrations of the taste receptor antagonist GIV3727 (known to be an antagonist at TAS2R31) and observing a decrease in the amplitude of the $[Ca^{2+}]_i$ signal with increasing concentrations of GIV3727. In this specific example, the assay can be performed, e.g., with primary human airway smooth muscle cells or with H292 cells, since both express TAS2R31.

In general, assays for agonists and antagonists of bitter taste receptors can be performed with any source of airway cells (e.g., airway smooth muscle cells or non-ciliated airway epithelial cells) that express one or more bitter taste receptors. For example, primary human airway smooth muscle cells can be obtained from human tissues as described in SA Green et al. (Influence of beta2-adrenergic receptor genotypes on signal transduction in human airway smooth muscle cells. *Am. J. Respir. Cell Mol. Biol.* 13:25-33, 1995), herein incorporated by reference in its entirety.

Another source of primary smooth muscle cells that can be used in the screening methods described herein is Catalogue No. CC-2576 (and others) from Lonza Research Solutions. In addition, as will be appreciated by the skilled artisan, Lonza is a source of normal and diseased airway epithelial cells and airway smooth muscle cells. Lonza also provides normal and diseased airway fibroblasts, which can also be used in the screening methods of the invention, as long as the cell type selected expresses one or more bitter taste receptor of interest.

Another cell line that is useful in the methods described herein is the immortalized human bronchial epithelial cell line BEAS-2B (American Type Culture Collection Catalogue No. CRL-9609). H292 (also known as NCI-H292; American Type Culture Collection Catalogue No. CRL-1848) are human lung mucoepidermoid carcinoma-derived derived cells that express multiple types of bitter taste receptors (see, e.g., Table 1). If appropriate, airway cells can also be tested using them within tracheal rings, as described herein and as is well-known in the art.

TABLE 1

Expression of mRNA for the bitter taste receptors in H292 cells by real-time PCR

| Receptor | Ratio CHRM3 |
|---|---|
| TAS2R14 | 1.040 ± .289 |
| TAS2R31 | 0.811 ± .326 |
| TAS2R10 | 0.755 ± .294 |
| TAS2R3 | 0.459 ± .260 |
| TAS2R38 | 0.437 ± .192 |
| TAS2R4 | 0.303 ± .126 |
| TAS2R5 | 0.301 ± .042 |
| TAS2R30 | 0.230 ± .154 |
| TAS2R46 | 0.205 ± .083 |
| TAS2R19 | 0.197 ± .135 |
| TAS2R1 | 0.186 ± .176 |
| TAS2R50 | 0.164 ± .093 |
| TAS2R8 | 0.102 ± .102 |
| TAS2R13 | 0.101 ± .037 |
| TAS2R40 | 0.096 ± .076 |
| TAS2R20 | 0.075 ± .050 |
| TAS2R43 | ND |
| TAS2R9 | ND |
| TAS2R39 | ND |
| TAS2R45 | ND |
| TAS2R7 | ND |
| TAS2R16 | ND |
| TAS2R42 | ND |
| TAS2R60 | ND |
| TAS2R41 | ND |
| CHRM3 | 1.0 (reference) |

Results are normalized to the expression of the M3-muscarinic receptor (CHRM3). ND, not detected; results are from 3-6 experiments)

In addition, any non-human cells can be used as appropriate, e.g., mouse or rat primary airway cells, used as primary cell isolates, established cell lines, or tracheal rings. Any other animal species can also be used as appropriate (including, but not limited to, dog, cow, pig, primate, etc.). The skilled artisan will understand how to identify the appropriate cell source for use in the herein-described methods.

EXAMPLES

Methods $[Ca^2]_i$, cAMP and Membrane Potential Measurements.

Primary human ASM cells were obtained from a commercial source (Clonetics) and maintained as described[31], with experiments performed using cells at passages 3-8. These cells consisted of >95% airway smooth muscle as previously ascertained[31]. For detecting changes in $[Ca^{2+}]_i$ attached cells in 96-well plates (80,000 cells/well) were loaded with Fluo-4 AM (BD Biosciences) with probenecid for one hour at 37° C. Receptor agonists were added at the indicated concentrations at 37° C. by an automated pipetting system in triplicate and the 525 nm signals were generated by excitation at 485 nm using a Flex Station II (Molecular Devices). Data was acquired every 1.5 sec for 60 sec. Unless otherwise stated, studies were performed in media containing 1.5 mM calcium. In some studies, ASM were transfected with T2R10 siRNA (Invitrogen) or a scrambled-sequence siRNA control by electroporation (Nucleofector, Lonza) using 4×10⁶ cells and 4 μg of siRNA. Twenty-four hours later cells were transferred to the 96-well plates for the $[Ca^{2+}]_i$ assay. For cAMP measurements, human ASM cells were plated in 24-well dishes, agonists added for the indicated times at 37° C. in triplicate, and the reaction stopped by addition of a lysis buffer and rapid freezing. Samples were acetylated and cAMP measured by a highly sensitive $^{125}$I-cAMP based radioimmunoassay as previously described[32]. VASP phosphorylation status was ascertained by Western blots of whole cell lysates using specific antibodies (Alexis Biochemicals) for the non-phosphorylated and phosphorylated forms. The effects of bitter tastants on membrane potential of whole ASM cells was measured using a membrane potential-sensitive fluorescent dye (Molecular Devices) as described[19] in a 96 well plate format with 50,000 cells/well. Excitation was at 530 nm and emission acquired at 565 nm. Data were collected in real time for 300 sec and are shown as relative fluorescent units.

Ex Vivo Intact Airway Physiology.

All mouse studies were approved by the Animal Care and Use Committee, and human tissue studies were approved by the Institutional Review Board, of the University of Maryland, Baltimore. From ~60-day old FVB/N mice, 5 mm sections of trachea were excised and studied in an isometric myograph system (Radnoti) as previously described[33]. Briefly, tracheal rings fitted between a fixed wire and a transducer-coupled wire were maintained in Krebs buffer at 37° C. with aeration from 95% $O_2$, 5% $CO_2$. A passive tension of 5 mN was established for each ring, which we have shown to provide an optimal length-tension relationship for studying contraction and relaxation from GPCR agonists[34]. Experiments were performed using a range of doses or single concentrations as indicated. When appropriate, wash-out of drug was accomplished by three 25 ml exchanges with Krebs buffer. For relaxation studies, rings were contracted with agents such as acetylcholine using a fixed concentration, which was maintained during addition of multiple doses of isoproterenol or bitter tastants. Fourth-order bronchi from freshly obtained human tissue from surgical specimens were dissected from regions without gross pathology, rings prepared and studied in a manner similar to that above.

Magnetic Twisting Cytometry.

Dynamic changes in baseline cell stiffness were measured as an indicator of contraction and relaxation of isolated human ASM cells using magnetic twisting cytometry as described in detail previously[15]. In brief, Arg-Gly-Asp coated ferromagnetic microbeads bound to adherent human ASM cells were magnetized horizontally and then twisted in a vertically aligned homogenous magnetic field that was varying sinusoidally in time. Sinusoidal twisting magnetic field caused both a rotation and a pivoting displacement of the bead: such forced bead motions are, in turn, impeded by internal stresses developed by the cell. Lateral bead displacements in response to the resulting oscillatory torque were detected with a spatial resolution of ~5 nm, and the ratio of specific torque to bead displacements was computed and expressed as the cell stiffness in units of Pascal/nm (Pa/nm). For each individual ASM cell, baseline stiffness was measured for the first 60 sec, and after drug addition stiffness was measured continuously for the next 540 sec. In some experiments, cells were pre-exposed to vehicle or inhibitors for 10 min (iberiotoxin 10 nM, charybdotoxin 10 nM, H89 100 nM, or U73122 1 µM) prior to addition of GPCR agonists. For each cell, stiffness was normalized to its baseline stiffness prior to the agonist stimulation.

Confocal Imaging of Regional and Local $[Ca^2]_i$ Signals.

Regional and local $[Ca^{2+}]_i$ signals were visualized as previously described[35,36] using the membrane permeable $[Ca^{2+}]_i$-sensitive fluorescent dye Fluo-3 acetoxymethyl ester (Fluo-3 AM). Cultured human ASM were loaded with 5 µM Fluo-3 AM (dissolved in DMSO with 20% pluronic acid) for 30-45 min at room temperature (~22° C.). Cells were washed with Tyrode solution containing (in mM) 137 NaCl, 5.4 KCl, 2 $CaCl_2$, 1 $MgCl_2$, 10 HEPES, and 10 glucose, pH 7.4 (adjusted with NaOH) to remove extracellular Fluo-3 AM, and rested for 15-30 min in a cell chamber to allow complete de-esterification of cytosolic dye. Fluo-3 AM was excited at 488 nm, and fluorescence was measured at >505 nm. Two dimension images were scanned at 0.22 µm/pixel, 512 pixels/line, 256 lines/image once every 0.5 s. Linescan images were collected at 0.075 µm/pixel, 512 pixels/line at 2 ms intervals for 10,000 lines/image. Images were processed with algorithms using the IDL software package. Fluorescence signals (F) of each confocal image were first background subtracted and normalized in terms of $F/F_0$, where $F_0$ is the baseline fluorescence before drug application. Amplitude of $[Ca^{2+}]_i$ signal were further calibrated to absolute $[Ca^{2+}]_i$ by a pseudo-ratio method[37]. Typical image fields contained 2-4 cells, and for each experiment 10 fields were examined.

T2R expression. Total RNA was extracted from human ASM cells and reverse transcription was carried out using 2 µg RNA, oligo dT primers, and Moloney Murine leukemia virus reverse transcriptase. Real time PCR was carried out using methods previously described in detail[38], with specific primers (Applied Biosystems) for the 25 T2Rs, the indicated other GPCRs, and GAPDH using an Applied Biosystems 7300 Real Time PCR system. Data were analyzed using the $\Delta\Delta C_T$ method with ADRB2 as the reference[39]. The PCR products derived from primers for T2R10, 14, 44, 5, 4, and 48 were sequenced and verified to be the indicated human T2Rs. Immunocytochemistry was carried out using fixed cells as described[31]. The antisera titers were: T2Rs (Thermo Scientific) 1:300, gustducin (Santa Cruz) 1:500 and $BK_{Ca}$ (Sigma) 1:100.

Ovalbumin Sensitization and Pulmonary Function Testing.

Sensitization of 6-week old BALB/c mice was carried out by i.p. injections of 100 pg ovalbumin in 200 µl alum, or alum alone (control) on days 0 and 14. Mice were then challenged with 1.0% aerosolized ovalbumin on days 19, 21 and 24. Twenty-four hours after the last challenge, mice were sedated, intubated and the flexiVent system (SCIREQ) was utilized for ventilation and measurement of airway resistance as previously described[40]. Ventilation was at 150 breaths/min with a tidal volume of 240 µl and positive end expiratory pressure of 2.5 cm $H_2O$. After stabilization, mice were challenged with doses of aerosolized methacholine (2.0, 4.0, 8.0 and 16 mg/ml in the nebulizer) until the sustained airway resistance became ~5-fold greater than baseline. Three minutes after the last acetylcholine inhalation, the bitter tastants quinine (150 µg) or denatonium (200 µg), or the β-agonist albuterol (3.0 µg) were administered by aerosol over 10 sec. Resistance measurements (Raw, cm $H_2O$/ml/sec) were taken every 30 sec throughout the experiment.

Statistical Analysis.

Dose response curves for $[Ca^{2+}]_i$ and ex vivo tracheal ring studies were analyzed by iterative non-linear (sigmoidal) least squares fitting. Results from all studies were compared using paired or unpaired two-way t-tests (depending on study design), with P<0.05 considered significant. When multiple comparisons were sought, an ANOVA with post-hoc t-tests was utilized with a correction for multiple comparisons. Data are presented as mean±standard error.

Results

Human ASM Express Bitter Taste Receptors Couple to $[Ca^{2+}]_i$.

Figure 1:
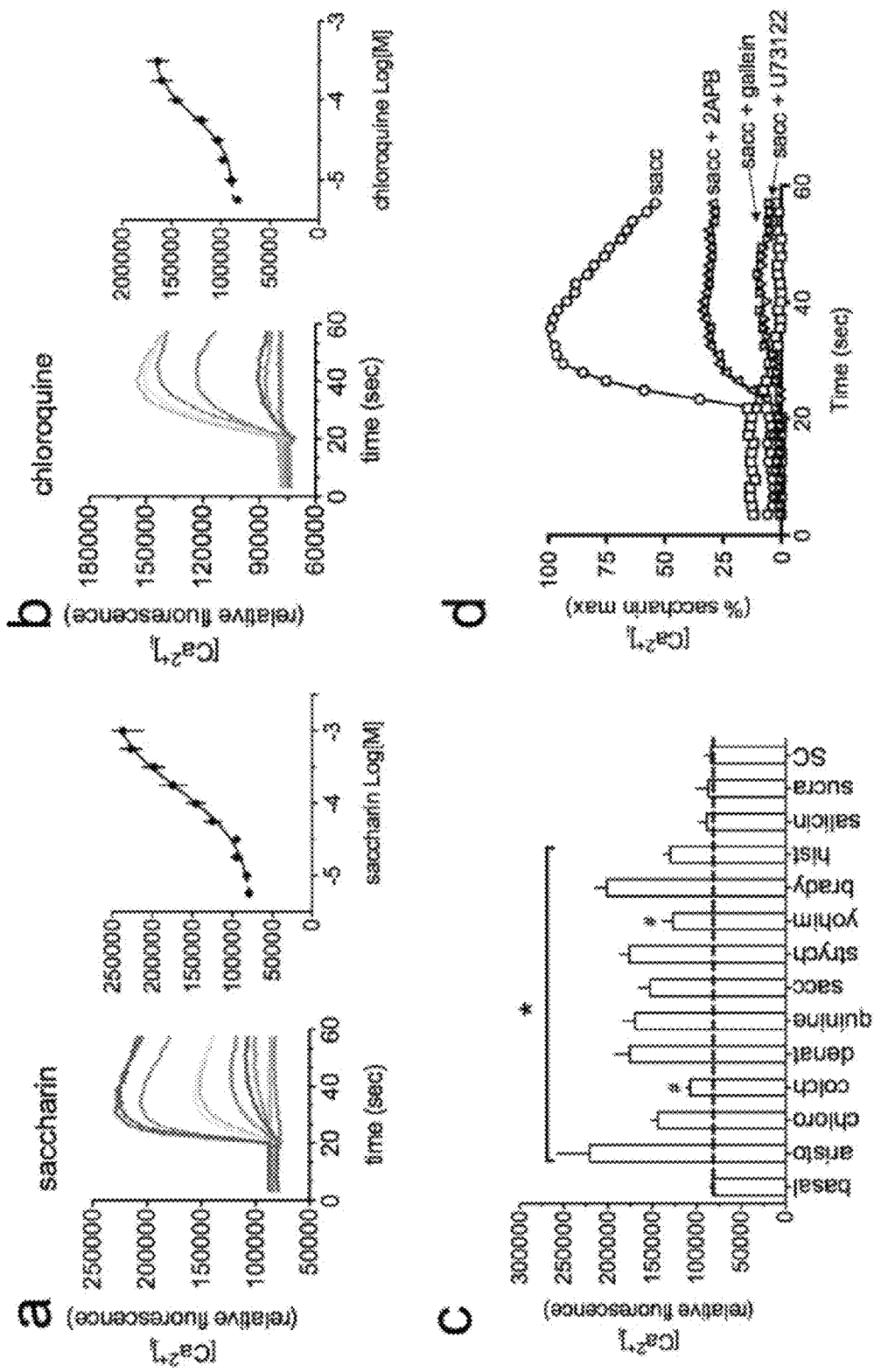
FIG. 1—Bitter tastants of diverse structures evoke increases in $[Ca^{2+}]_i$ in human airway smooth muscle cells.

Initial studies found that several known bitter taste receptor agonists (such as chloroquine, saccharin, and denatonium) evoked increased $[Ca^{2+}]_i$ in cultured human ASM cells (FIGS. 1a,b,c). The $[Ca^{2+}]_i$ responses in ASM cells to these bitter tastants were found to be similar in magnitude to those for known bronchoconstrictive GPCR agonists such as histamine and bradykinin (FIG. 1c). These results prompted quantitative RT-PCR studies with primers for all 25 known T2R genes, where we identified multiple bitter taste receptor transcripts expressed in human ASM. Expression was compared to levels of the gene for the $β_2$-adrenergic receptor ($β_2AR$), a receptor with recognized physiologic and pharmacologic relevance to regulation of ASM tone (Table 2—nomenclature as described in W. Meyerhof et al., Chem Senses 35: 157-170 (2010)). Also shown are the expression of two other GPCRs (ADORA1 and LTB4R) known to be expressed on human airway smooth muscle cells (ASM) at high and low levels, respectively. Table 3 provides the mRNA expression levels shown in Table 2, but instead uses an alternative nomenclature for bitter taste receptors that is well-known in the art. The differences in the two nomenclatures can be seen by comparing Tables 2 and 3.

TABLE 2 mRNA expression of bitter taste receptors in human ASM cells by real-time PCR

| Receptor | Ratio ADRB2 |
|---|---|
| T2R10 | 3.967 ± .893 |
| T2R14 | 3.519 ± .397 |
| T2R44 | 3.415 ± .498 |
| T2R5 | 1.767 ± .190 |
| T2R4 | 1.457 ± .271 |
| T2R48 | 1.372 ± .249 |
| T2R3 | 0.836 ± .079 |
| T2R49 | 0.710 ± .202 |
| T2R45 | 0.703 ± .118 |
| T2R50 | 0.482 ± .033 |
| T2R47 | 0.318 ± .060 |
| T2R9 | 0.315 ± .034 |
| T2R13 | 0.264 ± .037 |
| TAS2R55 | 0.263 ± .009 |
| TAS2R46 | 0.256 ± .041 |
| TAS2R1 | 0.179 ± .027 |
| TAS2R8 | 0.158 ± .007 |
| T2R39 | ND |
| T2R43 | ND |
| T2R7 | ND |
| T2R40 | ND |
| T2R16 | ND |
| T2R38 | ND |
| T2R41 | ND |
| T2R60 | ND |
| T1R1 | ND |
| T1R2 | ND |
| ADRB2 | 1.0 (reference) |
| ADORA1 | 2.434 ± .446 |
| LTB4R | 0.295 ± .056 |

Results are normalized to expressio of the ADRB2. ADORA1 and LTB4R represent high- and low-expressing GPCRs as positive controls, respectively.
ND, not detected. Results are from 4-6 experiments.

TABLE 3 mRNA expression of bitter taste receptors in human ASM cells by real-time PCR showing an alternative nomenclature for bitter taste receptors

| Receptor | Ratio ADRB2 |
|---|---|
| TAS2R10 | 3.96 ± .893 |
| TAS2R14 | 3.51 ± .397 |
| TAS2R31 | 3.41 ± .498 |
| TAS2R5 | 1.76 ± .190 |
| TAS2R4 | 1.45 ± .271 |
| TAS2R19 | 1.37 ± .249 |
| TAS2R3 | 0.83 ± .079 |
| TAS2R20 | 0.71 ± .202 |
| TAS2R45 | 0.70 ± .118 |
| TAS2R50 | 0.48 ± .033 |
| TAS2R30 | 0.31 ± .060 |
| TAS2R9 | 0.31 ± .034 |
| TAS2R13 | 0.26 ± .037 |
| TAS2R42 | 0.26 ± .009 |
| TAS2R46 | 0.25 ± .041 |
| TAS2R1 | 0.17 ± .027 |
| TAS2R8 | 0.15 ± .007 |
| TAS2R39 | ND |
| TAS2R43 | ND |
| TAS2R7 | ND |
| TAS2R40 | ND |
| TAS2R16 | ND |
| TAS2R38 | ND |
| TAS2R41 | ND |
| TAS2R60 | ND |
| TAS1R1 | ND |
| TAS1R2 | ND |
| ADRB2 | 1.0 (reference) |
| ADORA1 | 2.43 ± .446 |
| LTB4R | 0.29 ± .056 |

Results are normalized to expression of the ADRB2. ADORA1 and LTB4R represent high- and low-expressing GPCRs as positive controls, respectively.
ND, not detected. Results are from 4-6 experiments.

Multiple TAS2R transcripts were found to be expressed in human ASM, with the T2R10, T2R14 and T2R44 subtypes being the most highly expressed. Transcripts for two sweet receptors initially identified by the arrays[6] (T1R1 and T1R2) were not confirmed by RT-PCR (Table 2). Further screens with additional bitter tastants revealed $[Ca^{2+}]_i$ responses to aristocholic acid, strychnine, quinine, colchicine, and yohimbine (FIG. 1c). Importantly, we found no response to two sweet receptor agonists, sucralose and SC45647 (FIG. 1c). And, we note a relatively low response in ASM to colchicine which activates T2R4 (a mid-level ASM expressor by RT-PCR) and no response to salicin which exclusively activates T2R16[10] (which was not detected in ASM by RT-PCR). The robust response to strychnine (activates T2R10 and −46) is also consistent with T2R10 having high expression in ASM. Thus in ASM the $[Ca^{2+}]_i$ response to bitter tastants is concordant with a rank-order based on agonist specificity and the T2R subtype expression in these cells, and, there is no $[Ca^{2+}]_i$ response to sweet receptor agonists. Immunocytochemistry of human ASM cells using polyclonal antisera directed against two high expressing receptors (T2R10 and T2R44) and a receptor that was not detected by RT-PCR (T2R7) revealed cell surface expression of the former two receptors but not for the latter (FIG. 2). These studies also revealed expression of the α subunit of gustducin in these cells (FIG. 2).

Transfection of ASM cells with siRNA directed against T2R10 decreased T2R10 mRNA by 36±1.8% compared to the scrambled siRNA control, which was accompanied by a 26+2.0% decrease in strychnine-promoted $[Ca^{2+}]_i$ (P<0.05 vs. control). In additional studies, ASM cells were incubated with media alone or polyclonal antisera directed against T2R10, T2R7 or isotype-specific IgG and then strychnine-promoted $[Ca^{2+}]_i$ determined. T2R10 antisera decreased strychnine-promoted $[Ca^{2+}]_i$ responses in a dose-dependent manner (maximal inhibition of ~77%, FIG. 3) consistent with the RT-PCR and immunocytochemistry results showing expression of this T2R. As a control for nonspecific effects, antisera against T2R7 (which is not expressed in ASM) at the same titers had no significant effect on $[Ca^{2+}]_i$ stimulation, nor did IgG. Taken together, the above studies confirm expression of T2Rs on ASM cells and link expression to bitter tastant-mediated $[Ca^{2+}]_i$ signaling. The increase in $[Ca^{2+}]_i$ in human ASM cells elicited by saccharin was not dependent on the presence of extracellular $Ca^{2+}$, and the response was ablated by the Gβγ inhibitor gallein, the PLCβ inhibitor U73122, and partially inhibited by the inositol-3-phosphate ($IP_3$) receptor antagonist 2APB (FIG. 1d). These results in ASM cells are consistent with the signal transduction for bitter taste receptors in specialized taste cells of the tongue, where the $G_{gust}$-associated βγ activates PLCβ resulting in IP$_3$ generation which activates the IP$_3$ receptor on the sarco(endo)plasmic reticulum, releasing Ca$^{2+}$ from this intracellular store[9].

Bitter Taste Receptors Evoke Airway Relaxation.

Given that the increase in [Ca$^{2+}$]$_i$ promoted by some of the bitter tastants in human ASM was similar in magnitude to that of ligands acting on bronchoconstrictive GPCRs, we initially assumed that bitter taste receptors evoked ASM contraction. However, in isolated intact mouse airways, chloroquine, denatonium and quinine caused a dose-dependent relaxation, with a maximal response of >90% loss of the active contraction evoked by acetylcholine (FIG. 4a). The maximal relaxation response to the full β$_2$AR agonist isoproterenol under these same experimental conditions was a 30±9.2% reduction in active tension (FIG. 4a). Chloroquine and quinine were also studied with airways that were contracted by a different G$_q$-receptor agonist (serotonin, FIG. 4b), and marked relaxation was also observed. The EC$_{50}$s for chloroquine relaxation (93±4.3 μM and 110±32 μM) were nearly identical regardless of whether contraction was stimulated by acetylcholine or serotonin, respectively. In addition, we found that bitter tastants relaxed baseline tracheal ring tension by ~30% (FIG. 5). In a limited number of studies in fourth order bronchi obtained from non-diseased portions of human lung tissues, we also observed relaxation from 50-80% from chloroquine or saccharin on acetylcholine contracted rings (FIG. 6). Bitter tastant-mediated airway relaxation was not altered by the cyclooxygenase inhibitor indomethacin or the nitric oxide synthase inhibitor L-NAME, suggesting a direct activation of ASM receptors rather than a secondary response generated from bronchoactive ligands generated from airway epithelial cells. Airway relaxation observed with β-agonists is due to β$_2$AR coupling to an increase in cAMP with subsequent PKA activation[2]. However, we found no evidence for chloroquine-promoted increases in cAMP or PKA activation in intact cultured ASM cells, as assessed by a sensitive radioimmunoas say or by the PKA-mediated phosphorylation of vasodilator-stimulated phosphoprotein (VASP), respectively (FIG. 4c). In a set of serial dosing and washout experiments with intact airways, a submaximal dose of chloroquine resulted in ~67% relaxation of acetylcholine-mediated constriction, which was fully reversed by washout and re-challenge with acetylcholine (FIG. 4d). These airways were then exposed to a maximal concentration of isoproterenol, attaining 29±4.3% relaxation, a value similar to that obtained without any preexposure to chloroquine (FIG. 4a). Furthermore, exposure to both chloroquine and isoproterenol resulted in relaxation that was greater than that found with either compound alone (FIG. 4d). These data indicate that chloroquine-promoted relaxation is not due to cell injury since ASM functional contraction and relaxation are not impaired by pre-exposure to chloroquine, and, that the relaxation is additive to that of a β-agonist suggesting a different mechanism of relaxation.

Bitter Taste Receptors Relax ASM by Opening BK$_{Ca}$ Channels from Localized Ca$^{2+}$ Release.

Taken together, these paradoxical results showed that despite bitter taste receptor agonists evoking an increase in [Ca$^{2+}$]$_i$ in ASM, they act as bronchodilators, indeed, the most efficacious bronchodilators that we have ever found. While we had characterized the mechanism of these receptors' signaling to [Ca$^{2+}$]$_i$ in this cell-type, the coordinated airway response in the intact airway was not consistent with the expected bronchoconstriction. To further ascertain the mechanism by which bitter taste receptors evoke ASM relaxation, we used magnetic twisting cytometry[5] to measure dynamic changes in stiffness of isolated human ASM cells (FIG. 7), thus removing any potential confoundment from unrecognized mechanisms present in intact tissue. In these experiments magnetic particles attached to the cell by a peptide linker provide a highly quantitative measurement of single-cell stiffness, with isoproterenol and histamine exposure resulting in the expected relaxation and contraction from baseline, respectively (FIG. 7a).

Chloroquine and saccharin exposure (FIG. 7a) resulted in ASM relaxation at this single cell level, confirming that these bitter tastants act directly on smooth muscle cells, and consistent with our findings in the coordinated relaxation response of intact airways (FIG. 4a and FIG. 5). The relaxation response to saccharin was not blocked by the PKA inhibitor H89 (FIG. 7b) confirming results from cAMP and VASP phosphorylation measurements (FIG. 4c). Inhibition of PLC by U73122 eliminated the saccharin-promoted relaxation of isolated ASM (FIG. 7b). In light of our findings with PLC inhibition (as well as 137 inhibitors and IP$_3$ receptor antagonists) on bitter tastant-promoted increases in [Ca$^{2+}$]$_i$ (FIG. 1d), these results indicated that the relaxation response of these receptors in ASM is triggered by, or requires, intracellular Ca$^{2+}$ release. Consistent with this concept, the chloroquine EC$_{50}$ values for [Ca$^{2+}$]$_i$ release in cultured ASM cells (70±10 μM, FIG. 1a) and in the relaxation of intact airways (93±4.3 μM, FIG. 4a) are virtually identical.

The dependence of relaxation on SR Ca$^{2+}$ release was further supported by results of studies with the SR Ca$^{2+}$ re-uptake inhibitor thapsigargin, which depletes the SR of [Ca$^{2+}$]$_i$. Thapsigargin pre-incubation blocked chloroquine and other bitter tastant-mediated [Ca$^{2+}$]$_i$ stimulation in ASM cells (FIG. 8), and also chloroquine-mediated relaxation of intact airway rings (FIG. 9). A potential mechanism for Ca$^{2+}$-mediated relaxation in ASM is via hyperpolarization due to stimulation of the large conductance Ca$^{2+}$-activated K$^+$-channel (BK$_{Ca}$). These channels are known to be expressed on human ASM[16] (which we confirmed; FIG. 2) and have been reported to regulate airway tone[17]. To test whether the observed relaxation is due to bitter tastant-triggered Ca$^{2+}$ activation of BK$_{Ca}$, human ASM cells were pretreated with carrier, a Ca$^{2+}$-dependent K$^+$ channel antagonist charybdotoxin, or the specific BK$_{Ca}$ channel antagonist iberiotoxin. As shown in FIG. 7b, both pretreatments ablated saccharin-mediated ASM relaxation as assessed in isolated cells. Similar results were found with chloroquine. And finally, pretreatment with iberiotoxin also attenuated chloroquine-promoted relaxation in the isolated mouse airway (FIG. 7c).

The relaxation of ASM from BK$_{Ca}$ activation would be expected to be from membrane hyperpolarization[18]. ASM cells were loaded with a membrane potential-sensitive fluorescent dye[19], and as shown in FIG. 10a, exposure to KCl and histamine resulted in the expected membrane depolarization. With exposure to the bitter tastants chloroquine and saccharin, membrane hyperpolarization was readily observed. Furthermore, bitter tastant-promoted membrane hyperpolarization was completely inhibited by iberiotoxin (FIG. 10b). Thus the highly efficacious bronchodilator response from ASM bitter taste receptors appears to be due to [Ca$^{2+}$]$_i$-dependent activation of BK$_{Ca}$, which is distinct from histamine promoted increases in [Ca$^{2+}$]$_i$ which causes contraction. This suggested that the intracellular distribution of the Ca$^{2+}$ responses to histamine and bitter tastants are different, and indeed, it is established that a high concentration of localized [Ca$^{2+}$]$_i$ is associated with BK$_{Ca}$ activation[20].

To define the characteristics of saccharin-promoted $[Ca^{2+}]_i$ increases in ASM cells, real-time confocal imaging was performed in Fluo-3 loaded cells (FIG. 11). As shown, localized $[Ca^{2+}]_i$ signals were detected at the slender ends and sarcolemmal regions of ASM. This response was rapid (e.g., observed within 2.5 sec in the cross-sectional studies, FIG. 11a) and the magnitude was greater than at the central region of the myocytes (FIG. 11b). When using the line-scan mode at regions within 1 µm and parallel to the cell membrane of ASM cells, spatially and temporally discernible $[Ca^{2+}]_i$ events were detected very early after the application of saccharin, prior to the subsequent sustained localized rise in $[Ca^{2+}]_i$ (FIG. 11e). These results confirm the notion that saccharin promotes localized $[Ca^{2+}]_i$ signals in ASM cells. In contrast, the response to histamine in ASM cells caused a rapid rise in $[Ca^{2+}]_i$ throughout the cell (FIG. 11c), without the localized features observed with saccharin.

Bitter Tastants Counteract Bronchoconstriction in a Mouse Model of Asthma.

Collectively, the above results all pointed to a novel ASM relaxation pathway that might be utilized for treating reversible obstructive lung diseases such as asthma. To assess this potential, bitter tastants were administered by inhalation in the context of a mouse model of allergic airway inflammation and bronchial hyperresponsiveness. Mice were sensitized to ovalbumin and then repetitively challenged with inhaled ovalbumin, which resulted in acute airway inflammation (FIGS. 12a,b). Airway resistance was measured in these intact, sedated, intubated mice at baseline, after the response to inhalation of the bronchoconstrictor methacholine, and then after inhalation of bitter tastants during the bronchoconstrictive phase. The positive control for these studies was inhaled albuterol, a β-agonist that is the most commonly utilized bronchodilator in asthma therapy. In the ovalbumin-sensitized mice, the concentration of inhaled methacholine required to increase baseline airway resistance by 5-fold was 8 mg/ml, compared to 16 mg/ml for non-sensitized mice, confirming the airway hyperreactivity phenotype. Inhaled aerosolized quinine decreased airway resistance in normal and sensitized mice by 53±2.96% and 50±8%, respectively, indicating efficacy in a pathophysiologically relevant model of obstructive airway disease (FIGS. 12c,d). Bronchodilatory effects were also found with denatonium, amounting to 44±6% in the normal mice and 57±4% in the sensitized mice.

GPCRs expressed on ASM represent the major family of signaling receptors that regulate airway tone and caliber. Within the airway milieu in asthma, multiple locally generated ligands act on these receptors ultimately leading to bronchoconstriction. The pro-bronchoconstrictive GPCRs couple to $G_{\alpha q}$, increase $[Ca^{2+}]_i$, and trigger ASM contraction. In contrast, GPCRs coupled to $G_{\alpha s}$ increase cAMP, relax ASM and bronchodilate, with the $\beta_2$AR being the target for β-agonists, the most commonly utilized therapeutic for bronchospasm. Identification of novel ASM receptors that lead to bronchoconstriction and dilation further refines our understanding of the signaling network at play in asthma, and allows new therapeutic approaches. Here we unexpectedly found expression of several GPCRs belonging to the T2R bitter taste receptor family on human ASM. Given that bitter signaling has been thought to serve an aversion response, we assumed that ASM bitter taste receptors would act to contract the muscle leading to bronchoconstriction, with shortness of breath as the cue to escape from a noxious environment. Because these receptors respond to potentially hundreds of bitter ligands, this scenario seemed reasonable, in that discrimination of the specific ligand would not be necessary, rather only the generation of a signal that an inhalant is potentially harmful. These considerations are consistent with how bitter taste receptors of the tongue evolved due to poisonous plant toxins[9,13]. A recent report[21] has also identified bitter taste receptors on motile cilia of airway epithelial cells that increase beat frequency, considered a mechanical defense against noxious inhalants. These receptors are also found in the anterior nasal cavity where they promote sneezing and regulate respiratory rate[22], again repulsion-like responses to noxious stimuli. On the other hand, bitter taste receptors expressed on enteroendocrine cells of the gastrointestinal tract appear to promote homeostatic control of glucose levels[23]. By bronchodilating, bitter taste receptors on ASM may act in a compensatory manner to acyl-homoserine lactones which can be agonists at these receptors[24] and are secreted by Gram-negative bacteria[25] during bronchitis or pneumonia, thereby providing protection from bronchospasm. However, we initially considered that bitter taste receptors on ASM might be the basis for unexplained bronchospasm, such as is found with occupational asthma, based on the diverse nature of their agonists, and their coupling to $[Ca^{2+}]_i$ stimulation.

In studies of cultured ASM cells, this prediction of a constrictive response to bitter taste receptor ligands seemed inevitable, as the increase in $[Ca^{2+}]_i$ was similar to that from classic bronchoconstrictive GPCR activation, such as with histamine. However, in intact airways, these agents induced substantial relaxation, which was greater than the most efficacious bronchodilator which has ever been utilized clinically (the β-agonist isoproterenol). The effect was not due to cellular injury leading to loss of active contraction, as relaxation was readily reversible by washout, and post-exposure the airways contracted and dilated normally to methacholine and isoproterenol, respectively. The bitter tastants signaled to increased $[Ca^{2+}]_i$ via a PLCβ- and $IP_3$ receptor-dependent manner. Furthermore, bitter tastant activation of $[Ca^{2+}]_i$ was blocked by a Gβγ inhibitor, consistent with typical bitter taste receptor signal transduction via the gustducin-associated βγ subunit. The increased $[Ca^{2+}]_i$ from activation of this pathway would be expected to cause ASM constriction, such as that observed with $G_{\alpha q}$-coupled receptor stimulation of PLCβ.

We explored the potential for dual coupling of ASM bitter taste receptors to $Ca^{2+}$ and cAMP, which might explain the net relaxation in the face of increased $[Ca^{2+}]_i$. Such dual coupling has been described for the sweet receptors in pancreatic β-cells[26], and $\beta_2$AR have been reported to cause increases and decreases in $[Ca^{2+}]_i$ in smooth muscle[27,28]. However, in ASM cells we were unable to detect cAMP increases or PKA activation from bitter tastant exposure, and ASM relaxation from these tastants was not affected by the PKA inhibitor H89. Furthermore, the gustducin α subunit is thought to enhance phosphodiesterase activity[29], which if anything might decrease cAMP levels. Additional studies in the intact airway excluded two well-known bronchodilator pathways evoked from airway epithelial cells (cyclooxygenase products such as $PGE_2$, and, nitric oxide), and the single-cell mechanics of isolated ASM showed that the effect of bitter tastants was by direct action on ASM. Interestingly, the dose-response curves for $[Ca^{2+}]_i$ stimulation and ASM relaxation showed equivalent $EC_{50}$ values, suggestive of a connection between this intracellular response and the physiological response. And indeed, depletion of SR $Ca^{2+}$ resulted in the loss of bitter tastant-mediated increases in ASM cell $[Ca^{2+}]_i$, as well as the relaxation effect observed in intact airway rings. Confocal fluorescence imaging of $[Ca^{2+}]_i$ showed localized increases due to bitter tastants, which included early calcium events occurring within a distance of 1 μm to the cell surface. We considered bitter taste receptor-mediated, $[Ca^{2+}]_i$-dependent, opening of $BK_{Ca}$ because of this tight relationship between $[Ca^{2+}]_i$ and relaxation, the known expression of $BK_{Ca}$ on ASM, and its requirement for membrane-associated $[Ca^{2+}]_i$ for activation. And indeed, blockade of $BK_{Ca}$ ablated single cell relaxation, intact airway relaxation, and membrane hyperpolarization from bitter tastants. The basis for the restricted $[Ca^{2+}]_i$ response from bitter tastants remains to be defined. Interestingly, a small degree of depolarization was observed from bitter tastants in the context of $BK_{Ca}$ blockade, suggesting that the two calcium pools (histamine receptor-promoted vs. T2R-promoted) may have some overlap. Nevertheless, the net effect of histamine-mediated $[Ca^{2+}]_i$ increase is depolarization and contraction while for bitter tastants is hyperpolarization and relaxation. Finally, aerosolized administration of several bitter tastants relaxed the airways in a mouse model of allergic inflammation, indicating that the pathway has therapeutic relevance in a diseased state.

There is an unmet need for additional therapeutic options in the treatment of obstructive airway diseases such as asthma. While there has been some progress in refining drugs that antagonize a particular $G_q$-coupled pathway, thereby potentially decreasing bronchospasm, β-agonists remain the only practical direct bronchodilators. Here we show that agents which bind bitter taste receptors cause marked bronchodilation of intact airways which was ~3-fold greater than that promoted by β-agonist in vitro. Furthermore, the effect of bitter taste receptors appears to be additive to that of β-agonists, consistent with different mechanisms of action, and thus combination therapy can be used. This new class of bronchodilators may have additional benefits over β-agonists, as the bitter taste receptors lack sites for PKA-mediated receptor desensitization, and have few potential sites for G-protein coupled receptor kinase-mediated desensitization. Thus there may be less tachyphylaxis, or loss of the bronchoprotective effect, with a bitter taste receptor agonist compared to that observed with β-agonists[30].

All documents, books, manuals, papers, patents, published patent applications, guides, abstracts and other reference materials cited herein are incorporated by reference in their entirety and to the same extent as if each independent publication or patent application was specifically and individually indicated to be incorporated by reference.

While the invention has been described in connection with specific examples and embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

LITERATURE CITED

1. Vignola, A. M., Bonsignore, G., Chanez, P. & Bousquet, J. *Fatal Asthma* 139-155 (Marcel Dekker, Inc., New York, 1998).
2. Billington, C. K. & Penn, R. B. Signaling and regulation of G protein-coupled receptors in airway smooth muscle. *Respir. Res.* 4, 2-24 (2003).
3. Green, S. A. & Liggett, S. B. *The Genetics of Asthma* 67-90 (Marcel Dekker, Inc., New York, 1996).
4. Drazen, J. M., Silverman, E. K. & Lee, T. H. Heterogeneity of therapeutic responses in asthma. *Br. Med. Bull.* 56, 1054-1070 (2000).
5. Malmstrom, K. et al. Oral montelukast, inhaled beclomethasone, and placebo for chronic asthma. A randomized, controlled trial. Montelukast/Beclomethasone Study Group. *Ann. Intern. Med.* 130, 487-495 (1999).
6. Einstein, R. et al. Alternative splicing of the G protein-coupled receptor superfamily in human airway smooth muscle diversifies the complement of receptors. *Proc. Natl. Acad. Sci.* 105, 5230-5235 (2008).
7. Misior, A. M. et al. Glucocorticoid- and protein kinase A-dependent transcriptome regulation in airway smooth muscle. *Am. J. Respir. Cell Mol. Biol.* 41, 24-39 (2009).
8. Bosse, Y., Maghni, K. & Hudson, T. J. 1alpha,25-dihydroxy-vitamin D3 stimulation of bronchial smooth muscle cells induces autocrine, contractility, and remodeling processes. *Physiol. Genomics* 29, 161-168 (2007).
9. Meyerhof, W. Elucidation of mammalian bitter taste. *Rev. Physiol. Biochem. Pharmacol.* 154, 37-72 (2005).
10. Meyerhof, W. et al. The molecular receptive ranges of human TAS2R bitter taste receptors. *Chem. Senses* 35, 157-170 (2010).
11. Chandrashekar, J. et al. T2Rs function as bitter taste receptors. *Cell* 100, 703-711 (2000).
12. Adler, E. et al. A novel family of mammalian taste receptors. *Cell* 100, 693-702 (2000).
13. Chandrashekar, J., Hoon, M. A., Ryba, N. J. & Zuker, C. S. The receptors and cells for mammalian taste. *Nature* 444, 288-294 (2006).
14. Lombardo, L. J. & Balmes, J. R. Occupational asthma: a review. *Environ. Health Perspect.* 108 Suppl 4, 697-704 (2000).
15. An, S. S., Fabry, B., Trepat, X., Wang, N. & Fredberg, J. J. Do biophysical properties of the airway smooth muscle in culture predict airway hyperresponsiveness? *Am. J. Respir. Cell Mol. Biol.* 35, 55-64 (2006).
16. Martin, G. et al. Interleukin-4 activates large-conductance, calcium-activated potassium (BKCa) channels in human airway smooth muscle cells. *Exp. Physiol.* 93, 908-918 (2008).
17. Morin, C., Sirois, M., Echave, V., Gomes, M. M. & Rousseau, E. Functional effects of 20-HETE on human bronchi: hyperpolarization and relaxation due to BKCa channel activation. *Am. J. Physiol. Lung Cell. Mol. Physiol.* 293, L1037-L1044 (2007).
18. Kotlikoff, M. I. & Kamm, K. E. Molecular mechanisms of β-adrenergic relaxation of airway smooth muscle. *Annu. Rev. Physiol.* 58, 115-141 (1996).
19. Baxter, D. F. et al. A novel membrane potential-sensitive fluorescent dye improves cell-based assays for ion channels. *J. Biomol. Screen.* 7, 79-85 (2002).
20. Fakler, B. & Adelman, J. P. Control of K(Ca) channels by calcium nano/microdomains. *Neuron* 59, 873-881 (2008).
21. Shah, A. S., Ben Shahar, Y., Moninger, T. O., Kline, J. N. & Welsh, M. J. Motile cilia of human airway epithelia are chemosensory. *Science* 325, 1131-1134 (2009).
22. Finger, T. E. et al. Solitary chemoreceptor cells in the nasal cavity serve as sentinels of respiration. *Proc. Natl. Acad. Sci. U.S.A.* 100, 8981-8986 (2003).
23. Wu, S. V. et al. Expression of bitter taste receptors of the T2R family in the gastrointestinal tract and enteroendocrine STC-1 cells. *Proc. Natl. Acad. Sci. U.S.A.* 99, 2392-2397 (2002).
24. Brockhoff, A., Behrens, M., Massarotti, A., Appendino, G. & Meyerhof, W. Broad tuning of the human bitter taste receptor hTAS2R46 to various sesquiterpene lactones, clerodane and labdane diterpenoids, strychnine, and denatonium. *J. Agric. Food Chem.* 55, 6236-6243 (2007).

25. Sbarbati, A. et al. Acyl homoserine lactones induce early response in the airway. *Anat. Rec.* 292, 439-448 (2009).

26. Nakagawa, Y. et al. Sweet taste receptor expressed in pancreatic beta-cells activates the calcium and cyclic AMP signaling systems and stimulates insulin secretion. *PLoS ONE* 4, e5106 (2009).

27. Felbel, J., Trockur, B., Ecker, T., Landgraf, W. & Hofmann, F. Regulation of cytosolic calcium by cAMP and cGMP in freshly isolated smooth muscle cells from bovine trachea. *J. Biol. Chem.* 263, 16764-16771 (1988).

28. Yamaguchi, H., Kajita, J. & Madison, J. M. Isoproterenol increases peripheral [Ca2+]i and decreases inner [Ca2+]i in single airway smooth muscle cells. *Am. J. Physiol. Cell Physiol.* 268, C771-C779 (1995).

29. Yan, W. et al. Bitter taste transduced by PLC-beta(2)-dependent rise in IP(3) and alpha-gustducin-dependent fall in cyclic nucleotides. *Am. J. Physiol. Cell Physiol.* 280, C742-C751 (2001).

30. Liggett, S. B. & Green, S. A. *Beta$_2$-Agonists in Asthma Treatment* 19-34 (Marcel Dekker, Inc., New York, 1996).

31. Panebra, A., Schwarb, M. R., Glinka, C. B. & Liggett, S. B. Heterogeneity of transcription factor expression and regulation in human airway epithelial and smooth muscle cells. *Am. J. Physiol. Lung* 293, L453-L462 (2007).

32. Liggett, S. B. et al. Altered patterns of agonist-stimulated cAMP accumulation in cells expressing mutant β2-adrenergic receptors lacking phosphorylation sites. *Mol. Pharmacol.* 36, 641-646 (1989).

33. McGraw, D. W. et al. Airway smooth muscle prostaglandin-EP1 receptors directly modulate beta2-adrenergic receptors within a unique heterodimeric complex. *J. Clin. Invest.* 116, 1400-1409 (2006).

34. McGraw, D. W., Almoosa, K. F., Paul, R. J., Kobilka, B. K. & Liggett, S. B. Antithetic regulation by β-adrenergic receptors of Gq-receptor signaling via phospholipase-C underlies the airway β-agonist paradox. *J. Clin. Invest.* 112, 619-626 (2003).

35. Yang, X. R. et al. Multiple ryanodine receptor subtypes and heterogeneous ryanodine receptor-gated Ca2+ stores in pulmonary arterial smooth muscle cells. *Am. J. Physiol. Lung Cell Mol. Physiol.* 289, L338-L348 (2005).

36. Zhang, W. M. et al. ET-1 activates Ca2+ sparks in PASMC: local Ca2+ signaling between inositol trisphosphate and ryanodine receptors. *Am. J. Physiol. Lung Cell Mol. Physiol.* 285, L680-L690 (2003).

37. Cheng, H., Lederer, W. J. & Cannell, M. B. Calcium sparks: elementary events underlying excitation-contraction coupling in heart muscle. *Science* 262, 740-744 (1993).

38. Small, K. M. et al. Polymorphisms of the cardiac presynaptic α2Cadrenergic receptors: diverse intragenic variability with haplotype-specific functional effects. *Proc. Natl. Acad. Sci.* 101, 13020-13025 (2004).

39. Livak, K. J. & Schmittgen, T. D. Analysis of relative gene expression data using real-time quantitative PCR and the 2(-Delta Delta C(T)) Method. *Methods* 25, 402-408 (2001).

40. McGraw, D. W. et al. Crosstalk between Gi and Gq/Gs pathways in airway smooth muscle regulates bronchial contractility and relaxation. *J. Clin. Invest.* 117, 1391-1398 (2007).

What is claimed is:

1. A method of treating asthma in a subject, comprising administering a therapeutically effective amount of a pharmaceutical composition comprising a bitter tastant to a subject in need of treatment and having asthma, wherein the bitter tastant is selected from the group consisting of aristocholic acid, saccharin, and salicin, thereby treating the obstructive lung disease in the subject.

2. The method of claim 1, wherein the pharmaceutical composition is in the form of an inhalant.

3. The method of claim 1, wherein the subject is a human.

4. A method of inducing bronchodilation in a subject having asthma, comprising administering a therapeutically effective amount of a pharmaceutical composition comprising a bitter tastant to a subject in need of bronchodilation and having asthma, wherein the bitter tastant is selected from the group consisting of aristocholic acid, saccharin, and salicin, thereby inducing bronchodilation in the subject.

5. The method of claim 4, wherein the pharmaceutical composition is in the forr of an inhalant.

6. The method of claim 4, wherein the subject is a human.

7. A method of relaxing airway smooth muscle (ASM) in a subject having asthma, comprising administering a therapeutically effective amount of a pharmaceutical composition comprising a bitter tastant to a subject in need of ASM relaxation and having asthma, wherein the bitter tastant is selected from the group consisting of aristocholic acid, saccharin, and salicin, thereby relaxing the airway smooth muscle in the subject.

8. The method of claim 7, wherein the pharmaceutical composition is in the form of an inhalant.

9. The method of claim 7, wherein the subject is a human.

10. A method of treating bronchoconstriction or bronchospasm in a subject having asthma, comprising administering a therapeutically effective amount of a pharmaceutical composition comprising a bitter tastant to a subject in need of such treatment and having asthma, wherein the bitter tastant is selected from the group consisting of aristocholic acid, saccharin, and salicin, thereby treating the bronchoconstriction or bronchospasm.

11. The method of claim 10, wherein the pharmaceutical composition is in the form of an inhalant.

12. The method of claim 10, wherein the subject is a human.

13. A method for identifying a compound for relaxing airway smooth muscle, comprising contacting an airway smooth muscle cell with a test compound that binds to a bitter tastant receptor and determining whether the test compound relaxes the airway smooth muscle cell, wherein a compound that relaxes the smooth muscle cell is identified as a compound for relaxing airway smooth muscle.

14. The method of claim 13, wherein relaxation of the airway smooth muscle cell is detected by detecting an increase in bitter tastant receptor-mediated signaling in the airway smooth muscle cell.

15. The method of claim 14, wherein the increase in bitter tastant receptor-mediated signaling is detected by detecting an increase in intracellular calcium release or an increase in intracellular IP3 in the airway smooth muscle cell.

16. A method for identifying a modulator of a bitter taste receptor, comprising:

(a) contacting an airway cell that naturally expresses a bitter taste receptor with a test compound, wherein the airway cell is an airway smooth muscle cell or a non-ciliated airway epithelial cell, and (b) measuring the activity of the bitter taste receptor, wherein a compound that increases activity of the bitter taste receptor is an agonist of the bitter taste receptor and a compound that decreases activity of the bitter taste receptor is an antagonist of the bitter taste receptor.

17. The method of claim 16, wherein a change in activity of the bitter tastant receptor is detected by a change in intracellular calcium release or a change in intracellular IP3 in the airway cell, relative to an airway cell not contacted with the test compound.

18. A method for identifying a compound that is an antagonist of a bitter taste receptor, comprising:
  (a) contacting an airway cell that naturally expresses a bitter taste receptor with a test compound and with a bitter tastant, wherein the airway cell is an airway smooth muscle cell or a non-ciliated airway epithelial cell, and
  (b) measuring activity of the bitter taste receptor,
  wherein a test compound that inhibits activity of the bitter taste receptor compared to the activity of the bitter taste receptor in a cell contacted with the bitter tastant but not contacted with the test compound, identifies an antagonist of the bitter taste receptor.

19. The method of claim 18, wherein the activity of the bitter taste receptor is measured by measuring a change in intracellular calcium release or a change in intracellular IP3.

20. The method of claim 18, wherein the test compound is added before, after, or simultaneously with the bitter tastant.

* * * * *